United States Patent
Shetty

(10) Patent No.: US 10,478,465 B2
(45) Date of Patent: Nov. 19, 2019

(54) HERBAL COMPOSITION FOR THE TREATMENT AND MANAGEMENT OF CANCER AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: Muniyal Ayurvedic Research Centre, Manipal (IN)

(*) Notice: Subject to any disclaimer, the term of this patent is extended or adjusted under 35 U.S.C. 154(b) by 0 days.

(21) Appl. No.: 16/149,336

(22) Filed: Oct. 2, 2018

(65) Prior Publication Data

US 2019/0030104 A1    Jan. 31, 2019

Related U.S. Application Data

(63) Continuation-in-part of application No. 15/945,389, filed on Apr. 4, 2018.

(60) Provisional application No. 62/482,558, filed on Apr. 6, 2017.

(51) Int. Cl.

| | |
|---|---|
| A61K 36/24 | (2006.01) |
| A61P 35/00 | (2006.01) |
| A61K 35/04 | (2006.01) |
| A61K 36/264 | (2006.01) |
| A61K 36/28 | (2006.01) |
| A61K 36/9066 | (2006.01) |
| A61K 45/06 | (2006.01) |
| A61K 36/48 | (2006.01) |
| A61K 36/77 | (2006.01) |
| A61K 36/714 | (2006.01) |
| A61K 36/81 | (2006.01) |
| A61K 36/61 | (2006.01) |
| A61K 36/67 | (2006.01) |
| A61K 36/59 | (2006.01) |
| A61K 33/00 | (2006.01) |
| A61K 33/26 | (2006.01) |
| A61K 33/30 | (2006.01) |
| A61K 9/20 | (2006.01) |
| A61K 33/28 | (2006.01) |
| A61K 36/185 | (2006.01) |

(52) U.S. Cl.
CPC ............. *A61K 36/24* (2013.01); *A61K 9/205* (2013.01); *A61K 33/00* (2013.01); *A61K 33/26* (2013.01); *A61K 33/28* (2013.01); *A61K 33/30* (2013.01); *A61K 35/04* (2013.01); *A61K 36/185* (2013.01); *A61K 36/264* (2013.01); *A61K 36/28* (2013.01); *A61K 36/48* (2013.01); *A61K 36/59* (2013.01); *A61K 36/61* (2013.01); *A61K 36/67* (2013.01); *A61K 36/714* (2013.01); *A61K 36/77* (2013.01); *A61K 36/81* (2013.01); *A61K 36/9066* (2013.01); *A61K 45/06* (2013.01); *A61P 35/00* (2018.01)

(58) Field of Classification Search
CPC ........ A61K 33/00; A61K 33/26; A61K 33/30; A61K 35/04; A61K 36/24; A61K 36/264; A61K 36/28; A61K 36/48; A61K 36/59; A61K 36/61; A61K 36/67; A61K 36/714; A61K 36/77; A61K 36/81; A61K 36/9066; A61K 45/06; A61P 35/00
See application file for complete search history.

(56) References Cited

U.S. PATENT DOCUMENTS

2002/0136783 A1    9/2002  Singh et al.

FOREIGN PATENT DOCUMENTS

IN          200701734 12    *  3/2008    ............. A61K 36/54

OTHER PUBLICATIONS

Zhang et al (Nat Prod Res, 2013, vol. 27, pp. 1911-1916, abstract) (Year: 2013).*
Chaudhary, IN 200500769 I2, Derwent English abstract from East, Mar. 24, 2006 (Year: 2006).

* cited by examiner

*Primary Examiner* — Mark V Stevens
(74) *Attorney, Agent, or Firm* — Pilloff & Passino LLP; Sean A. Passino; Rachel K. Pilloff

(57) ABSTRACT

Herbal composition for the treatment and management of cancer and method of preparation are disclosed herein. The disclosed composition includes a combination of herb and mineral components that facilitate in inhibiting abnormal cell proliferation. The embodiments of the composition can thus be used in treatment of cancer and related morbidities. Also, disclosed herein is a method for inducing cytotoxicity in cancer cells.

29 Claims, 15 Drawing Sheets

HERBAL COMPOSITION FOR THE TREATMENT AND MANAGEMENT OF CANCER AND METHOD OF PREPARATION THEREOF

CROSS REFERENCE TO RELATED APPLICATION

This application is a continuation-in-part of the U.S. application Ser. No. 15/945,389 which in turn claims priority of the U.S. provisional application 62/482,558 filed on 6 Apr. 2017, the contents of which are incorporated herein by reference.

TECHNICAL FIELD

The embodiments disclosed in this specification relate to herbal composition effective in treatment and management of cancer and associated complications. It also relates to the process for preparation of such composition.

BACKGROUND

Cell proliferation is a highly mechanized activity controlled by an efficient regulatory system. Most cells are in a non-proliferative state unless they are stimulated. The loss of proliferative control leads to undesired abnormal cell proliferation and accumulation. Such accumulation caused by the subversion of proliferative control leads to tumorous outgrowths ultimately resulting in Cancer. Cancer can be of various types such as sarcoma, lymphoma, leukemia, melanoma, etc., depending on the type of cell that may be affected.

Cancer is by far one of the most dreaded diseases. It is considered to be a leading cause of death worldwide. For years, pharmaceutical industries and research institutes have been making best efforts in finding an effective treatment for cancer.

Modern medicine offers various methods for treating cancer including chemotherapy, radiation therapy, hormone therapy, targeted therapy etc. The type of treatment opted depends on location and stage of cancer. Although, evolutionary changes have occurred over the years in finding a treatment for cancer, these methods have been observed to have drawbacks. These commonly used treatment methods tend to affect healthy tissue, in addition to cancer tissues, thereby resulting in side effects such as Alopecia, Lymphedema, Pain, Bleeding, Bruising, Edema, Skin and Nail changes, Fertility problems, etc. These side effects in turn have adverse effects on patients, at a physical, mental, emotional and social level.

An alternate system of medicine, such as Ayurveda has often been resorted to by patients and is believed to provide promising results in treating cancer and it various complications while alleviating the undesirable side effects of treatment by modern medicine. Ayurveda is believed to offer a holistic approach in cancer treatment incorporating lifestyle and diet changes in addition to medication, thereby improving the mental and physical state of an individual as a whole. With the knowledge of the anti-tumor properties of herbs such as *Silybum marianum, Aloe barbadensis, Curcuma longa, Zingiber officinale, Hydrastis Canadensis* and *Annona muricata*, numerous herbal compositions have been developed for treatment and management of Cancer. Although these compositions have shown to have beneficial effects in cancer treatment, there still exists a need for a holistic and effective method of treating abnormal cell proliferation leading to cancer thus playing a more significant role in prevention, management and treatment of the disease.

OBJECT OF THE DISCLOSED EMBODIMENTS

The principal object of the embodiments disclosed herein is to provide a composition and method of treating cancer.

Another object of the embodiments disclosed herein is to provide a composition and method of inducing cytotoxicity and growth inhibitory effect in cancerous cells.

Further, it is also an object of the embodiments disclosed herein is to provide a composition and method for treatment of Cancer.

Another object of the embodiments disclosed herein is to provide a composition and method for management of Cancer.

Another object of the embodiments disclosed herein is to provide a composition and method for alleviating the side effect of Cancer treatment.

Another object of the embodiments disclosed herein is to provide a composition and method for preparing the human body to endure cancer treatment.

Yet another object of the embodiments disclosed herein is to provide herbal composition and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings. The embodiments herein will be better understood from the following description with reference to the drawings, in which.

SUMMARY

Figure 1A:
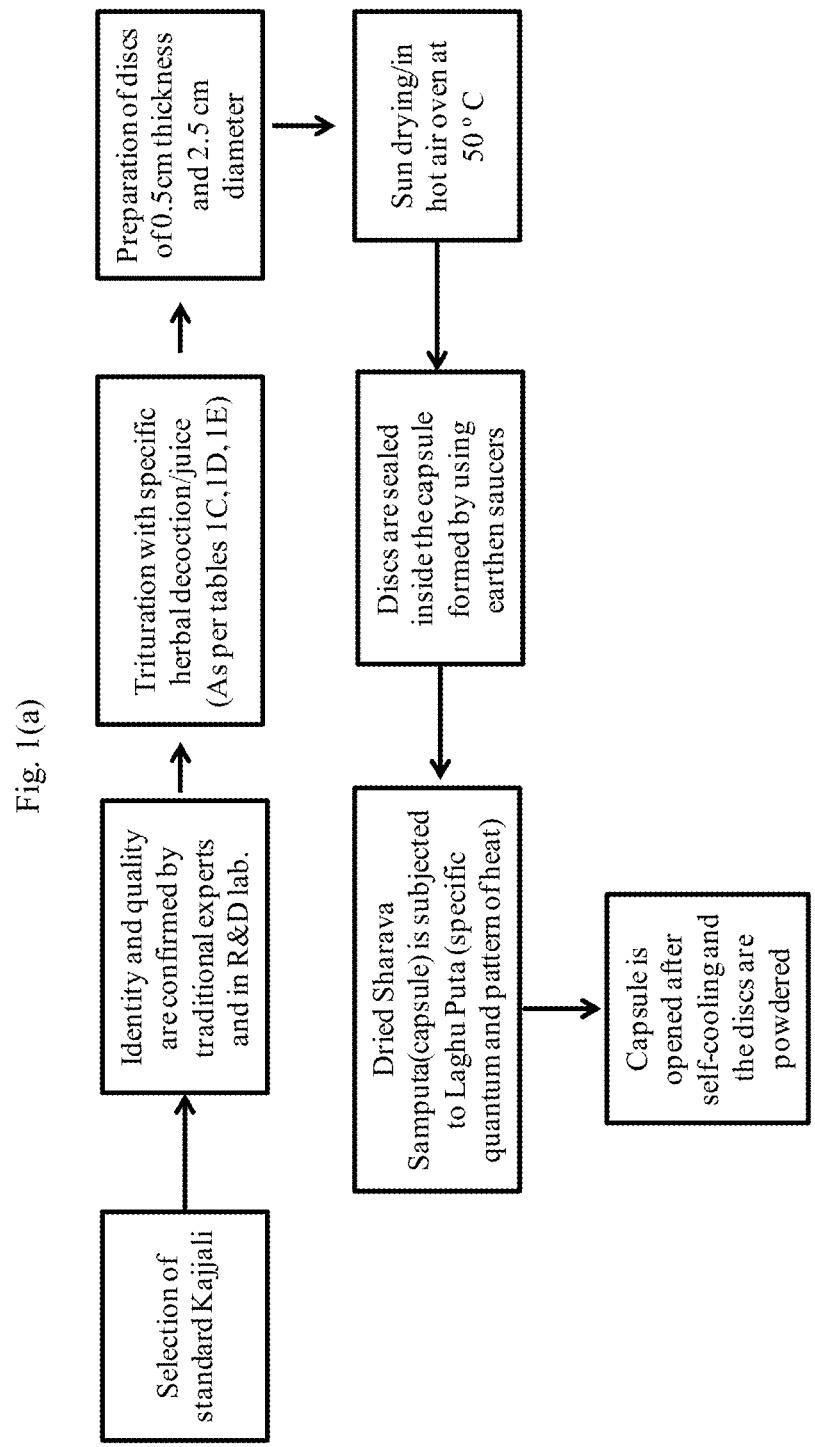
FIG. 1(a) depicts a flowchart for the preparation of Kajjali (processed black sulphide of mercury), according to the various embodiments herein.

The embodiments disclosed herein provide herbal compositions for the treatment and management of cancer. One embodiment comprises a composition of *Vinca rosea, Aristolochia indica, Eclipta alba, Moringa oleifera, Curcuma longa* or extracts thereof; and Kajjali; wherein each of *Vinca rosea, Aristolochia indica, Eclipta alba, Moringa oleifera* and *Curcuma longa* are present in an amount ranging from 3 to 6 wt % and Kajjali is present in an amount ranging from 0.1 to 20 wt % of the total weight of the composition.

Another embodiment provides for a composition that additionally comprises at least one of the following ingredients *Boerhavia diffusa* in an amount in the range of 1 to 3 wt %, *Adhatoda vasica* in an amount in the range of 2 to 4 wt %, *Bauhinia variegata* in an amount of ≤2 wt %, *Commiphora mukul* in an amount of 1 to 3 wt %, *Azadirachta indica* in an amount of ≤2 wt %, *Aconitum heterophyllum* in an amount of ≤2 wt %, *Smilax china* in an amount of ≤2 wt %, *Tinospora cordifolia* in an amount in the range of 1 to 3 wt %, *Withania somnifera* in an amount in the range of 1 to 3 wt %, *Sida cordifolia* in an amount in the range of 1 to 3 wt %, *Terminalia chebula* in an amount of ≤2 wt %, *Terminalia bellerica* in an amount of ≤2 w %, *Emblica officinalis* in an amount in the range of 2 to 4 wt %, *Tinospora cordifolia* in an amount of ≤2 wt %, *Piper longum* in an amount of ≤2 wt %, *Piper nigrum* in an amount of ≤2 wt %, *Zingiber officinalis* in an amount of ≤2 wt % and *Ocimum* sanctum in an amount in the range of 2 to 4 wt %, of the total weight of the composition.

In another embodiment, the composition further comprises *Asphaltum punjabianum* (Shilajit) in an amount in the range of 1 to 3 wt %, Vanga Bhasma in an amount of ≤2 wt %, Yashada Bhasma in an amount of ≤2 wt %, Swarna Makshika bhasma in an amount in the range of 1 to 3 wt %, Abhraka Bhasma in an amount in the range of 1 to 3 wt %, Loha bhasma in an amount in the range of 1 to 3 wt % and Pravala bhasma in an amount in the range of 1 to 3 wt %, of the total weight of the composition. A further embodiment additionally includes excipients, flavoring agents and colorants, preservatives and pH adjuster. One embodiment of the composition disclosed herein is in the form of a Tablet. In another embodiment, the composition disclosed herein is in the form of a 500 mg Tablet.

One of the embodiments disclosed herein, is manufactured by a process that comprises levigating Kajjali, bhasmas and shilajit, adding finely powdered herbs, and adding grinding decoction while continuing grinding to obtain the composition; wherein bhasmas may be selected from a group of bhasmas consisting of Vanga Bhasma, Yashada Bhasma, Swarna Makshika bhasma, Abhraka Bhasma, Loha bhasma, and Pravala bhasma; and finely powdered herbs comprises of *Vinca rosea* (dry leaves), *Aristolochia indica* (dry root), *Eclipta alba* (dry whole plant), *Moringa oleifera* (dry stem bark), *Curcuma longa* (dry rhizome), *Boerhavia diffusa* (dry root), *Adhatoda vasica* (dry root), *Bauhinia variegata* (dry stem bark), *Commiphora mukul* (oleo gum resin), *Azadirachta indica* (dry stem bark), *Aconitum heterophyllum* (dry root), *Smilax china* (dry root), *Tinospora cordifolia* (starch extract of stem), *Withania somnifera* (dry root), *Sida cordifolia* (dry root), *Terminalia chebula* (dry fruits), *Terminalia bellerica* (dry fruit), *Emblica officinalis* (dry fruits), *Tinospora cordifolia* (dry stem), *Piper longum* (dry fruits), *Piper nigrum* (dry fruits), *Zingiber officinalis* (dry rhizome) and *Ocimum* sanctum (dry leaves); and wherein said grinding decoction is a decoction of at least one herb selected from a group consisting of *Aegle marmelos, Premna mucronata, Oroxylum indicum, Stereospermum suaveolens, Gmelina arborea, Solanum indicum, Solanum xanthocarpum, Tribulus terrestris, Uraria picta, Desmodium gangeticum, Vinca rosea, Ocimum sanctum, Asparagus racemosus, Semecarpus anacardium, Momordica charantia, Eclipta alba, Moringa oleifera, Acacia catechu, Rubia cordifolia, Adhatoda vasica, Bauhinia variegata, Cynodon dactylon, Tinospora cordifolia, Crotalaria juncea, Cuminum cyminum, Smilax china, Mimosa pudica, Calotropis procera, Murraya koenigii, Trichosanthes dioica* and *Sida cordifolia*.

Another embodiment is manufactured by the process which further comprises of mixing the obtained composition with gum acacia and grinding, drying, and wet-granulating; wherein grinding may be performed for a period of 1 to 4 hours; and drying may be performed at a temperature of 45 to 55 degree Celsius.

Furthermore, some of the embodiments disclosed herein are instrumental in inducing cytotoxic/growth inhibitory effect in cancer cells. In one embodiment, the method for inducing cytotoxic/growth inhibitory effect in cancer cells comprises of administering cancer cells with embodiments of the herbal composition disclosed herein. In another embodiment, the method of treating cancer comprises of administering a therapeutically effective amount of an embodiment of the composition; wherein the therapeutically effective amount is in the range of 500 mg to 1000 mg per day. In another embodiment, the therapeutically effective amount includes an amount in the range of 500 mg to 1000 mg, administered about 1 to 3 times a day. The various embodiments of the composition disclosed herein may also be administered along with at least one other cancer medication. The other cancer medication includes allopathic and ayurvedic medication generally known in the treatment of cancer and may vary depending on the type of cancer.

Furthermore, these embodiments can be used in preparation of a medicament for treatment of cancer; in the preparation of a medicament as an anti-proliferative and growth inhibitory agent for cancer cells; and in the preparation of cytotoxic and apoptotic agent for cancer cells.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those skilled in the art to practice the embodiments herein. Accordingly, the examples should not be construed as limiting the scope of the embodiments herein.

The embodiments herein achieve a herbal composition of therapeutic value, and a process for the preparation of the composition. The herbal composition disclosed in the various embodiments herein show anti-cancer properties and therefore finds use in the prevention, management and treatment of cancer. The disclosed composition in various embodiments herein is instrumental in inducing cancer cell cytotoxicity and apoptosis. It has further been observed, in various embodiments, to have anti-proliferative and growth inhibitory effect on cancerous cells.

The composition disclosed in the various embodiments herein may be used in treating any type of cancer. It may be used to improve the general health of individuals having a condition involving abnormal, unregulated cell proliferation such as carcinoma of oesophagus, carcinoma of lung, bronchogenic carcinoma, adenocarcinoma of endometrium, adenocarcinoma of rectum, Non-Hodgkin's lymphoma, chronic myeloid leukemia, borderline mucinous tumor, adenocarcinoma of colon, fibro sarcoma, ovarian carcinoma, carcinoma of pancreas etc. Accordingly, the embodiments herein achieve a method for the treatment of Cancer. Also, disclosed are embodiments of a method of inhibition of abnormal cell proliferation.

Composition

The disclosed embodiments herein provide a herbal composition having a combination of selected herbs and minerals. In an embodiment, the herbal composition includes a herb component and a mineral component. In another embodiment, the herbal composition includes a herb component, a mineral component and a suitable excipient.

Herb Component

In an embodiment, the herb component includes the herbs *Vinca rosea, Aristolochia indica, Eclipta alba, Moringa oleifera* and *Curcuma longa*, or their extracts, or the active ingredients extracted from these herbs. In another embodiment, the herb component further includes at least one of the herbs selected from *Boerhavia diffusa, Adhatoda vasica, Bauhinia variegata, Commiphora mukul, Azadirachta indica, Aconitum heterophyllum, Smilax china, Tinospora cordifolia, Withania somnifera, Sida cordifolia, Terminalia chebula, Terminalia bellerica, Emblica officinalis, Tinospora cordifolia, Piper longum, Piper nigrum, Zingiber officinalis* and *Ocimum sanctum* or their extracts, or the active ingredients extracted from these herbs.

In an embodiment, the herb component may include specific parts of the herb (also referred as herb component) such as roots, fruits, stem, leaves, rhizome, etc. In an embodiment, the herb component may include leaves of *Vinca rosea*, roots of *Aristolochia indica*, whole plant of *Eclipta alba*, stem bark of *Moringa oleifera*, rhizome of *Curcuma longa*, roots of *Boerhavia diffusa*, roots of *Adhatoda vasica*, stem bark of *Bauhinia variegata*, oleo gum resin of *Commiphora mukul*, stem bark of *Azadirachta indica*, roots of *Aconitum heterophyllum*, roots of *Smilax china*, stem of *Tinospora cordifolia*, roots of *Withania somnifera*, roots of *Sida cordifolia*, fruits of *Terminalia chebula*, fruits of *Terminalia bellerica*, fruits of *Emblica officinalis*, starch extract of stem *Tinospora cordifolia*, fruit of *Piper longum*, fruit of *Piper nigrum*, rhizome of *Zingiber officinalis* and leaves of *Ocimum sanctum* or their extract. However, it is also within the scope of the claims provided herein for the herbal composition to include other herb components such as leaf, flowers, etc. without otherwise deterring intended function of the herbal composition.

The herb component maybe included in the composition in any form that is generally known in the field. For example, the herb component may be dried, powdered, processed to form concentrates, extracts, etc. In one preferred embodiment, the herb components are dried and powdered which is further incorporated into the composition.

In an embodiment, the herb component includes *Vinca rosea* in an amount ranging from 3 to 6 wt %, *Aristolochia indica* in an amount ranging from 3 to 6 wt %, *Eclipta alba* in an amount ranging from 3 to 6 wt %, *Moringa oleifera* in an amount ranging from 3 to 6 wt %, *Curcuma longa* in an amount ranging from 3 to 6 wt %, *Boerhavia diffusa* in an amount ranging from 1 to 3 wt %, *Adhatoda vasica* in an amount ranging from 2 to 4 wt %, *Bauhinia variegata* in an amount of ≤2 wt %, *Commiphora mukul* in an amount ranging from 1 to 3 wt %, *Azadirachta indica* in an amount of ≤2 wt %, *Aconitum heterophyllum* in an amount of ≤2 wt %, *Smilax china* in an amount of ≤2 wt %, *Tinospora cordifolia* in an amount of ≤3 wt %, *Withania somnifera* in an amount ranging from 1 to 3 wt %, *Sida cordifolia* in an amount ranging from 1 to 3 wt %, *Terminalia chebula* in an amount of ≤2 wt %, *Terminalia bellerica* in an amount of ≤2 w %, *Emblica officinalis* in an amount ranging from 2 to 4 wt %, *Piper longum* in an amount of ≤2 wt %, *Piper nigrum* in an amount of ≤2 wt %, *Zingiber officinalis* in an amount of ≤2 wt % and *Ocimum sanctum* in an amount ranging from 2 to 4 wt %, of the total weight of the composition.

Mineral Component

In an embodiment, the mineral component includes black sulphide of mercury (Kajjali). In another embodiment, the black sulphide of mercury (Kajjali) may be processed Kajjali. In another embodiment, the mineral component further includes Bhasmas or calcined preparations such as Swarna Makshika bhasma, Abhraka bhasma, Loha bhasma, Vanga bhasma, Yashada bhasma and Pravala bhasma. Alternatively, the mineral component may also be selected from a group consisting of at least one of mica, tin, zinc, coral, iron and copper pyrite. In the disclosed embodiments, the bhasmas along with the herb component form bioavailable herbal complexes which are useful in treating cancer. In another embodiment, the mineral component includes Shilajit. However, it is also within the scope of claims provided herewith for the herbal composition to include, as a substitute or additionally, other similar calcined preparations or minerals without otherwise deterring from the intended function of the herbal composition.

In an embodiment, the mineral component includes Kajjali (black sulphide of mercury) in an amount in the range of 0.1 to 20 wt %. In an embodiment, the mineral component includes shilajit in an amount in the range of 1 to 3 wt %. In another embodiment, the mineral component includes Abhraka Bhasma in an amount in the range of 1 to 3 wt %, Vanga Bhasma in an amount of ≤2 wt %, Pravala Bhasma in an amount in the range of 1 to 3 wt %, Loha Bhasma in an amount in the range of 1 to 3 wt %, Yashada bhasma in an amount of ≤2 wt %, and Swarna Makshika Bhasma in an amount in the range of 1 to 3 wt %, of the total weight of the composition.

The disclosed composition, in the various embodiments herein, may further include a suitable excipient. The suitable excipients include solvents, binders, lubricants, herbal carriers, oils and salts that are generally known in the art. In a preferred embodiment, the excipient includes acacia gum.

Further, the amount of each of herb component and mineral component that may be included in the various embodiments of the disclosed composition may be in the range of 0 to 30 wt % of the total weight of the composition. In an embodiment, the composition includes *Vinca rosea* (3 to 6 wt %), *Aristolochia indica* (3 to 6 wt %), *Eclipta alba* (3 to 6 wt %), *Moringa oleifera* (3 to 6 wt %), *Curcuma longa* (3 to 6 wt %), *Boerhavia diffusa* (1 to 3 wt %), *Adhatoda vasica* (2 to 4 wt %), *Bauhinia variegata* (≤2 wt %), *Commiphora mukul* (1 to 3 wt %), *Azadirachta indica* (≤2 wt %), *Aconitum heterophyllum* (≤2 wt %), *Smilax china* (≤2 wt %), *Tinospora cordifolia* (≤3 wt %), *Withania somnifera* (1 to 3 wt %), *Sida cordifolia* (1 to 3 wt %), *Terminalia chebula* (≤2 wt %), *Terminalia bellerica* (≤2 w %), *Emblica officinalis* (2 to 4 wt %), *Piper longum* (≤2 wt %), *Piper nigrum* (≤2 wt %), *Zingiber officinalis* (≤2 wt %) and *Ocimum sanctum* (2 to 4 wt %), Kajjali (black sulphide of mercury) (0.1 to 20 wt %), shilajit (1 to 3 wt %), Abhraka Bhasma (1 to 3 wt %), Vanga Bhasma (≤2 wt %), Pravala Bhasma (1 to 3 wt %), Loha Bhasma (1 to 3 wt %), Yashada bhasma (≤2 wt %), and Swarna Makshika Bhasma (1 to 3 wt %).

Further, the amount of gum acacia may be any amount suitable to perform the activity of an excipient. In an embodiment, the composition may include gum acacia in the range of 0 to 50 mg per 500 mg of the composition, preferably 8 to 10 wt % of the total weight of the composition.

However, it is apparent that slight variations in the amount of the ingredients may be performed without otherwise deterring from the intended function of the herbal composition.

The herbal composition disclosed herein may be formulated in various dosage forms such that it is suitable for oral administration. The herbal composition may be in the form of tablets, pellets, lozenges, granules, capsules, solutions, emulsions, suspensions, or any other form suitable for use. In an embodiment, the herbal composition is formulated in the form of tablets, preferably 500 mg tablets. For example: Table 1 depicts the quantities of each ingredient in a 500 mg tablet. All weight percentages are based on the total weight of the composition.

Further disclosed herein, is a tablet for treating cancer. In an embodiment, the tablet is a 500 mg tablet having herb component, mineral component and excipient as depicted in Table 1.

TABLE 1

Each 500 mg tablet includes:

| No | Sanskrit Name | Part used | Latin/English name | Quantity (in mg) | Quantity (in wt %) |
|---|---|---|---|---|---|
| 1 | Punarnava | Dried root | *Boerhavia diffusa* | 12 mg | 2.4 |
| 2 | Vasa | Dried root | *Adhatoda vasica* | 16 mg | 3.2 |
| 3 | Sadapushpa | Dried leaves | *Vinca rosea* | 24 mg | 4.8 |
| 4 | Kanchanara | Dried stem bark | *Bauhinia variegate* | 08 mg | 1.6 |
| 5 | Guggulu | Purified Oleo gum resin | *Commiphora mukul* | 12 mg | 2.4 |
| 6 | Nimba | Dried stem bark | *Azadirachta indica* | 08 mg | 1.6 |
| 7 | Ativisha | Dried root | *Aconitum heterophyllum* | 08 mg | 1.6 |
| 8 | Ishwari | Dried root | *Aristolochia indica* | 24 mg | 4.8 |
| 9 | Madhusnuhi | Dried root | *Smilax china* | 08 mg | 1.6 |
| 10 | Bhrngaraja | Dried whole plant | *Eclipta alba* | 24 mg | 4.8 |
| 11 | Guduchi Satva | Starch extract of stem | *Tinospora cordifolia* | 12 mg | 2.4 |
| 12 | Ashvagandha | Dried root | *Withania somnifera* | 12 mg | 2.4 |
| 13 | Bala | Dried root | *Sida cordifolia* | 12 mg | 2.4 |
| 14 | Hareetakee | dry fruits | *Terminalia chebula* | 04 mg | 0.8 |
| 15 | Vibhitaki | dried fruits | *Terminalia bellerica* | 04 mg | 0.8 |
| 16 | Amalaki | dried fruits | *Emblica officinalis* | 16 mg | 3.2 |
| 17 | Shilajatu | Fossil resin | *Asphaltum punjabicanum* | 12 mg | 2.4 |
| 18 | Guduchi | Dried stem | *Tinospora cordifolia* | 08 mg | 1.6 |
| 19 | Pippali | Dried fruit | *Piper longum* | 04 mg | 0.8 |
| 20 | Maricha | Dried fruit | *Piper nigrum* | 04 mg | 0.8 |
| 21 | Shunthi | Dried rhizome | *Zingiber officinalis* | 04 mg | 0.8 |
| 22 | Shigru | Dried stem bark | *Moringa oleifera* | 24 mg | 4.8 |
| 23 | Tulasi | Dried leaves | *Ocimum sanctum* | 16 mg | 3.2 |
| 24 | Haridra | Dried rhizome | *Curcuma longa* | 24 mg | 4.8 |
| 25 | Vanga Bhasma | Incinerated tin | Stanni oxidum | 06 mg | 1.2 |
| 26 | Yashada Bhasma | Incinerated zinc | Zinci oxidum | 06 mg | 1.2 |

TABLE 1-continued

Each 500 mg tablet includes:

| No | Sanskrit Name | Part used | Latin/English name | Quantity (in mg) | Quantity (in wt %) |
|---|---|---|---|---|---|
| 27 | Swarna Makshika bhasma | Incinerated copper pyrite | *Oxidum copper pyrite* | 12 mg | 2.4 |
| 28 | Abhraka Bhasma | Incinerated mica | *Mica oxidum* | 12 mg | 2.4 |
| 29 | Loha bhasma | Mineral | Incinerated Iron(ferric oxide) | 12 mg | 2.4 |
| 30 | Pravala bhasma | Mineral | Coral calx(calcium carbonate) | 12 mg | 2.4 |
| 31 | Processed Kajjali | Processed mineral compound | Processed Black sulphide of mercury | 100 mg | 20 |
| 32 | Excipient | Gum | *Gum acacia* | 40 mg | 8 |

Method

Disclosed herein are embodiments of a method of preparing the herbal composition. In an embodiment, the method includes, levigating processed Kajjali in a grinder;

adding finely powdered herbs into the grinder; and adding grinding decoction while continuing grinding to obtain the composition.

In another embodiment, the method includes, levigating processed Kajjali, bhasmas and shilajit in a grinder;

adding finely powdered herbs into the grinder; and adding grinding decoction while continuing grinding to obtain the composition.

In an embodiment, the process further includes mixing the obtained composition with an excipient such as gum acacia and grinding for a period of 1 to 4 hours; and drying of the obtained mass at a temperature in the range of 40 to 60 degree Celsius. Further, the obtained mass may be subjected to wet granulation followed by punching into 500 mg tablets.

The bhasmas include at least one of Abhraka Bhasma, Vanga Bhasma, Pravala Bhasma, Loha Bhasma, Yashada Bhasma and Swarna Makshika Bhasma. The mixture of Kajjali, bhasmas and Shilajit may be in semi solid form. In an embodiment, the levigation may be performed for a duration of around 3 hours.

Further, the finely powdered herbs include finely powdered dry root of *Boerhavia diffusa*, dry root of *Adhatoda vasica*, *Vinca rosea*, dry stem bark of *Bauhinia variegata*, oleo gum resin of *Commiphora mukul*, dry stem bark of *Azadirachta indica*, dry root of *Aconitum heterophyllum*, dry root of *Aristolochia indica*, dry root of *Smilax china*, dry whole plant of *Eclipta alba*, starch extract of stem *Tinospora cordifolia*, dry root of *Withania somnifera*, dry root of *Sida cordifolia*, dry fruit of *Terminalia chebula*, dry fruit of *Terminalia bellerica*, dry fruit of *Emblica officinalis*, dry stem of *Tinospora cordifolia*, dry fruit of *Piper longum*, dry fruit of *Piper nigrum*, dry rhizome of *Zingiber officinalis*, dry stem bark of *Moringa oleifera*, dry leaves of *Ocimum sanctum* and dry rhizome of *Curcuma longa*. In an embodiment, finely powdered herbs may be obtained by powdering and sieving the herb components at 80 mesh.

The grinding decoction is a decoction of selected herbs (also referred as grinding herbs). In an embodiment, the grinding decoction is a decoction of one or more herbs selected from a group consisting of: *Aegle marmelos*, *Premna mucronata*, *Oroxylum indicum*, *Stereospermum suaveolens*, *Gmelina arborea*, *Solanum indicum*, *Solanum xanthocarpum*, *Tribulus terrestris*, *Uraria picta*, *Desmodium gangeticum*, *Vinca rosea*, *Ocimum sanctum*, *Asparagus racemosus*, *Semecarpus anacardium*, *Momordica charantia*, *Eclipta alba*, *Moringa oleifera*, *Acacia catechu*, *Rubia cordifolia*, *Adhatoda vasica*, *Bauhinia variegata*, *Cynodon dactylon*, *Tinospora cordifolia*, *Crotalaria juncea*, *Cuminum cyminum*, *Smilax china*, *Mimosa pudica*, *Calotropis procera*, *Murraya koenigii*, *Trichosanthes dioica* and *Sida cordifolia*.

The decoction may be obtained by any method of decocting generally known in the field. In an embodiment, the method of preparation of grinding decoction includes:

soaking the grinding herbs. For example, soaking powdered dried roots of *Aegle marmelos*, *Premna mucronata*, *Oroxylum indicum*, *Stereospermum suaveolens*, *Gmelina arborea*, *Uraria picta*, *Desmodium gangeticum*, *Solanum indicum* and *Solanum xanthocarpum*, dried fruit of *Tribulus terrestris* fresh leaves of *Vinca rosea*, fresh leaves of *Ocimum sanctum*, fresh roots of *Asparagus racemosus*, purified nut of *Semecarpus anacardium*, fresh fruit of *Momordica charantia*, fresh whole plant of *Eclipta alba*, dried stem bark of *Moringa oleifera*, dried heartwood of *Acacia catechu*, dried root of *Rubia cordifolia*, fresh leaves of *Adhatoda vasica*, dried stem bark of *Bauhinia variegata*, fresh whole plant of *Cynodon dactylon*, fresh stem of *Tinospora cordifolia*, fresh leaves of *Crotalaria juncea*, dried cremocarp of *Cuminum cyminum*, dried root of *Smilax china*, dried whole plant of *Mimosa pudica*, dried root of *Calotropis procera*, fresh leaves of *Murraya koenigii*, dried whole plant of *Trichosanthes dioica* and dried root of *Sida cordifolia*; and concentrating the soaked herb mixture.

In an embodiment, soaking may be performed by soaking the grinding herbs in 16 parts of water overnight. In a further embodiment, concentrating may be performed by boiling at high temperature, preferably about 80° C. to 85° C., until ⅛th of the liquid remains. Concentration may be confirmed with the help of Brix meter.

Figure 2:
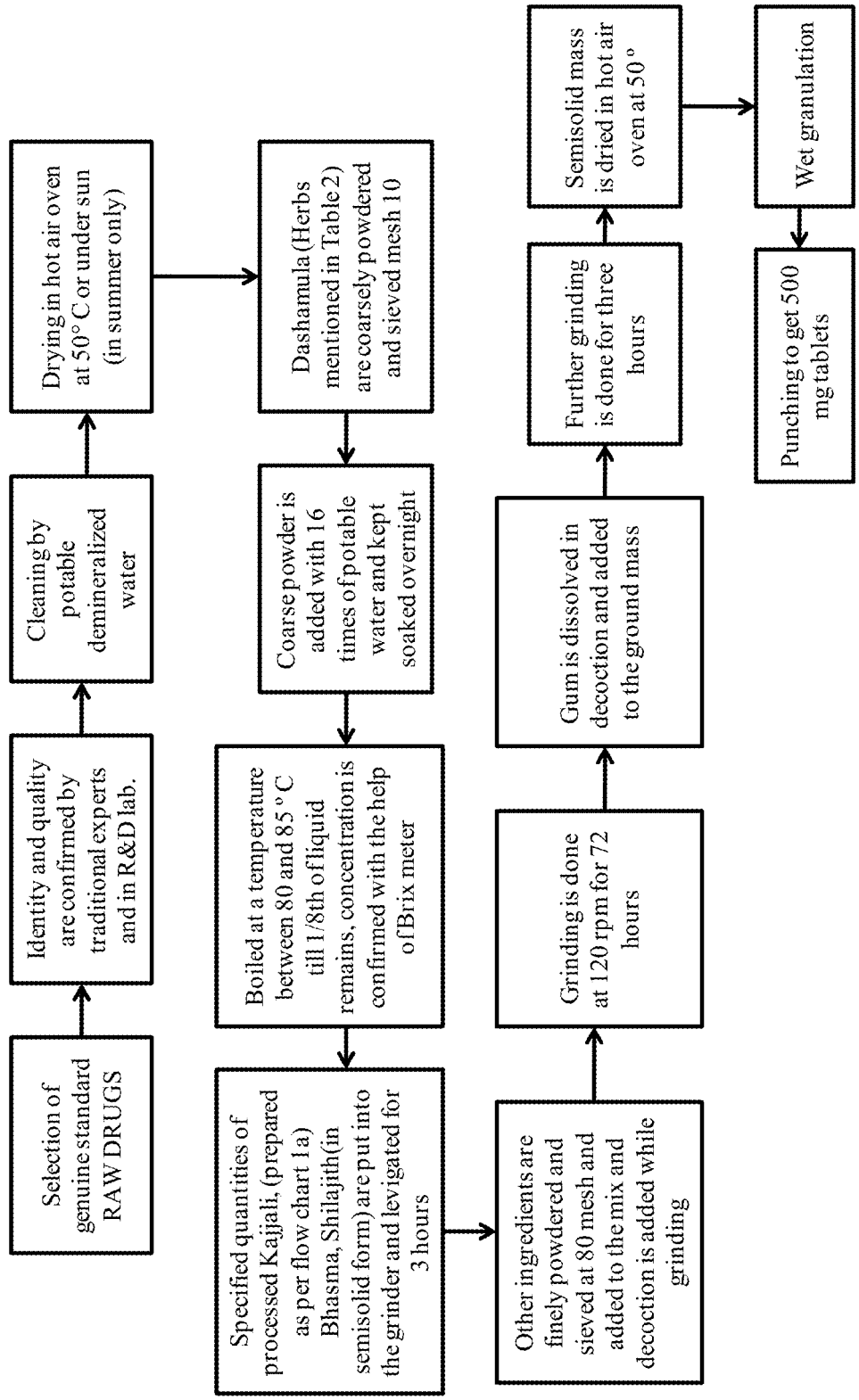
FIG. 2 depicts a flowchart for the preparation of fortified tablets, according to the various embodiments herein.

Further, once the grinding decoction is added, grinding is continued. In an embodiment, grinding is continued for about 72 hours, preferably at 120 rpm, to obtain a ground mass. In an embodiment, the method of preparation may further include adding excipient to the ground mass, wherein gum acacia may be added to the ground mass by dissolving in the grinding decoction while continuing grinding for 3 hours to obtain a semisolid mass. The method of preparation may further include drying at 50° C.-60° C., preferably in a hot air oven, wet granulating, punching to obtain 500 mg tablets. FIG. 2 depicts a flowchart for the preparation of fortified tablets. Table 2 depicts an embodiment of the Herbs required for grinding (grinding herbs).

TABLE 2

Dashamula Kashaya (Decoction of 10 herbs)

| | | | |
|---|---|---|---|
| 1. | Bilva dried root | *Aegle marmelos* | 1 part |
| 2. | Agnimantha dried root | *Premna mucronata* | 1 part |
| 3. | Shyonaka dried root | *Oroxylum indicum* | 1 part |
| 4. | Patala dried root | *Steriospermum suaveolens* | 1 part |
| 5. | Gambhari dried root | *Gmelina arborea* | 1 part |
| 6. | Brihati dried root | *Solanum indicum* | 1 part |
| 7. | Kantakari dried root | *Solanum xanthocarpum* | 1 part |
| 8. | Gokshura dried fruit | *Tribulus terrestris* | 1 part |
| 9. | Prishniparni dried root | *Uraria picta* | 1 part |
| 10. | Shalaparni dried root | *Desmodium gangeticum* | 1 part |
| 11. | Sadapushpa fresh leaves | *Vinca rosea* | 1 part |
| 12. | Tulasi fresh leaves | *Ocimum sanctum* | 1 part |
| 13. | Shatavari fresh roots | *Asparagus racemosus* | 1 part |
| 14. | Bhallataka purified nut | *Semecarpus anacardium* | 1 part |
| 15. | Karavellaka fresh fruit | *Momordica charantia* | 1 part |
| 16. | Bhringaraja fresh whole plant | *Eclipta alba* | 1 part |
| 17. | Shigru dried stem bark | *Moringa oleifera* | 1 part |
| 18. | Khadira dried heartwood | *Acacia catechu* | 1 part |
| 19. | Manjishtha dried root | *Rubia cordifolia* | 1 part |
| 20. | Vasa fresh leaves | *Adhatoda vasica* | 1 part |
| 21. | Kanchanara dried stem bark | *Bauhinia variegate* | 1 part |
| 22. | Durva fresh whole plant | *Cynadon dactylon* | 1 part |
| 23. | Guduchi fresh stem | *Tinospora cordifolia* | 1 part |
| 24. | Shanapushpi fresh leaves | *Crotolaria juncea* | 1 part |
| 25. | Jeeraka dried cremocarp | *Cuminumcyminum* | 1 part |
| 26. | Madhusnuhi dried root | *Smilax china* | 1 part |
| 27. | Lajjalu dried whole plant | *Mimosa pudica* | 1 part |
| 28. | Arka dried root | *Calatropis procera* | 1 part |
| 29. | Kaidarya fresh leaves | *Murraya koeinigi* | 1 part |
| 30. | Patola dried whole plant | *Trichosanthes dioica* | 1 part |
| 31. | Bala dried root | *Sida cordifolia* | 1 part |
| 32. | Jala | Water | 496 pats |
| | Avashesha (Reduced to) | | ⅛ part |

The Kajjali that is used in the various embodiments of the disclosed composition may be in the crude or processed form. In an embodiment, kajjali is in the processed form. Kajjali may be processed by various methods known in the field. In an embodiment, the method of processing Kajjali includes triturating Kajjali with specific herb decoction/juices, preparing into discs; drying of discs; preparing sharavasam puta, subjecting Sharavasam puta to Gaja puta, and powdering of discs once cooled. In an embodiment, the specific herb decoction/juices used to process Kajjali includes dried root of *Boerhavia diffusa*, fresh whole plant *Mimosa pudica*, fresh leaves *Piper betle*, fresh whole plant of *Amaranthus spinosus*, fresh leaves of *Piper longum*, whole plant of *Cynodon dactylon* and cow urine (Gomutra). Details of the herb decoction/juice used in processing Kajjali are provided hereunder by way of illustration only and should not be construed to limit the scope of the claims herewith. Table 3 depicts the herbs used in decoction form for grinding. Table 4 depicts the herbs used in fresh juice form for grinding. Table 5 depicts the liquid used for grinding. FIG. 1(a) depicts a flowchart for the processing of Kajjali.

TABLE 3

Kashaya (decoction) for grinding:
Decoction of following herbs:

| | | | |
|---|---|---|---|
| 1. | Punamava dried root | *Boerhavia diffusa* | 1 Part |
| | Jala | Water | 16 parts |
| | Avashesha (Reduced to) | | ⅛ part of water |

TABLE 4

Swarasa (fresh juice) for grinding:
Fresh juice of following herbs:

| | | | |
|---|---|---|---|
| 1. | Lajjalu fresh whole plant | *Mimosa pudica* | 1 Part |
| 2. | Nagavalli fresh leaves | *Piper betle* | 1 Part |
| 3. | Meghanada fresh whole plant | *Amaranthus spinosus* | 1 Part |
| 4. | Pippali fresh leaves | *Piperlongum* | 1 Part |
| 5. | Durva whole plant | *Cynadon dactylon* | 1 Part |

TABLE 5

Special liquid for grinding

| | | | |
|---|---|---|---|
| 1. | Gomutra | Cow urine | 1 Part |

The bhasmas that are used in the various embodiments of the disclosed herbal composition may be prepared by methods that are generally known in the field. In an embodiment, bhasmas may be prepared by selecting genuine standard minerals as starting material such as Swarna makshika, Mica, Iron, etc; drying in a hot air oven; purifying the mineral by triturating, quenching, boiling, etc; triturating with herbal decoction/juices; preparing into discs; drying of discs; preparing sharavasam puta, subjecting Sharavasam puta to Kukkuta/Gaja puta, and powdering of discs once cooled. In an embodiment, the method is repeated 30 times till bhasma is obtained.

Figure 1B:
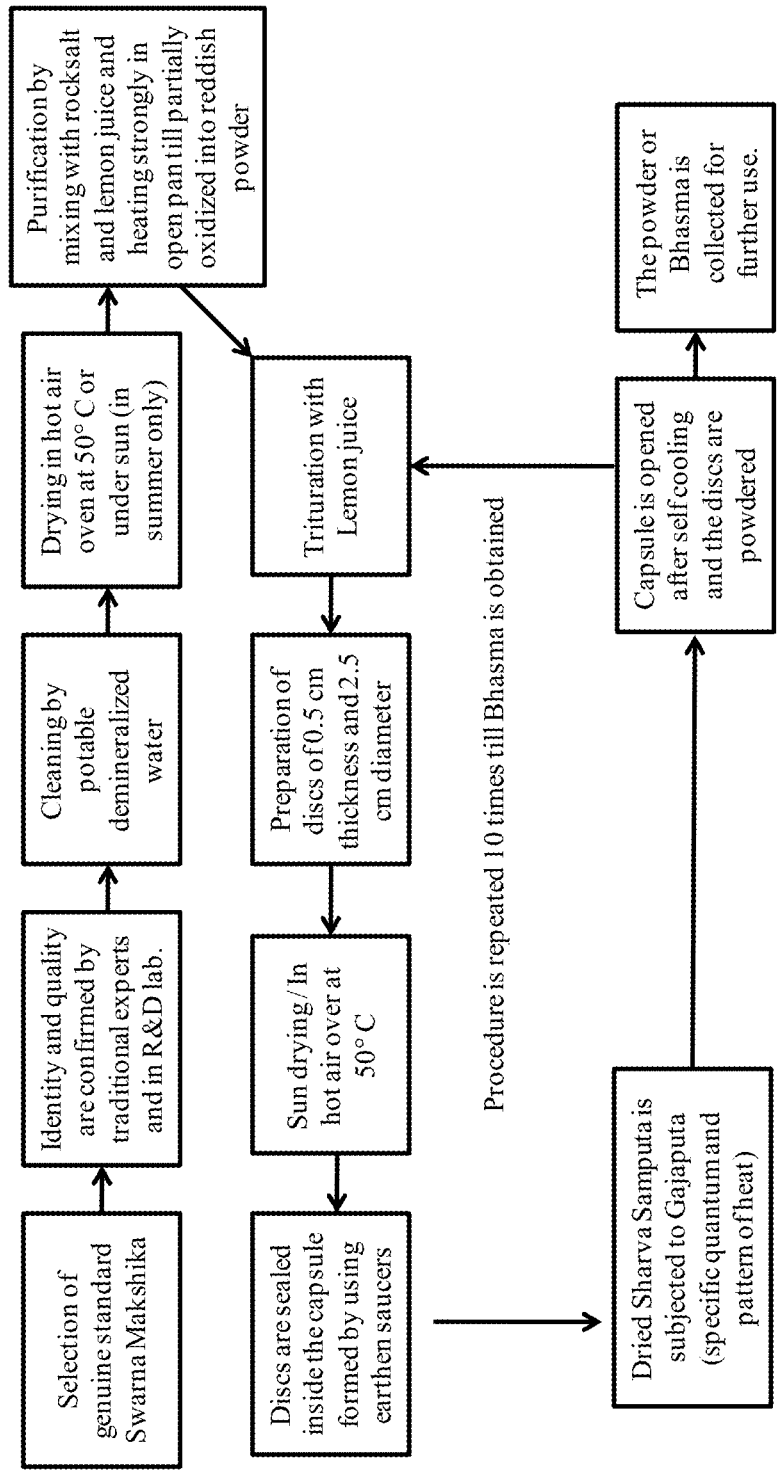
FIG. 1(b) depicts a flowchart for the preparation of Swarna Makshika Bhasma, according to the various embodiments herein.
Figure 1C:
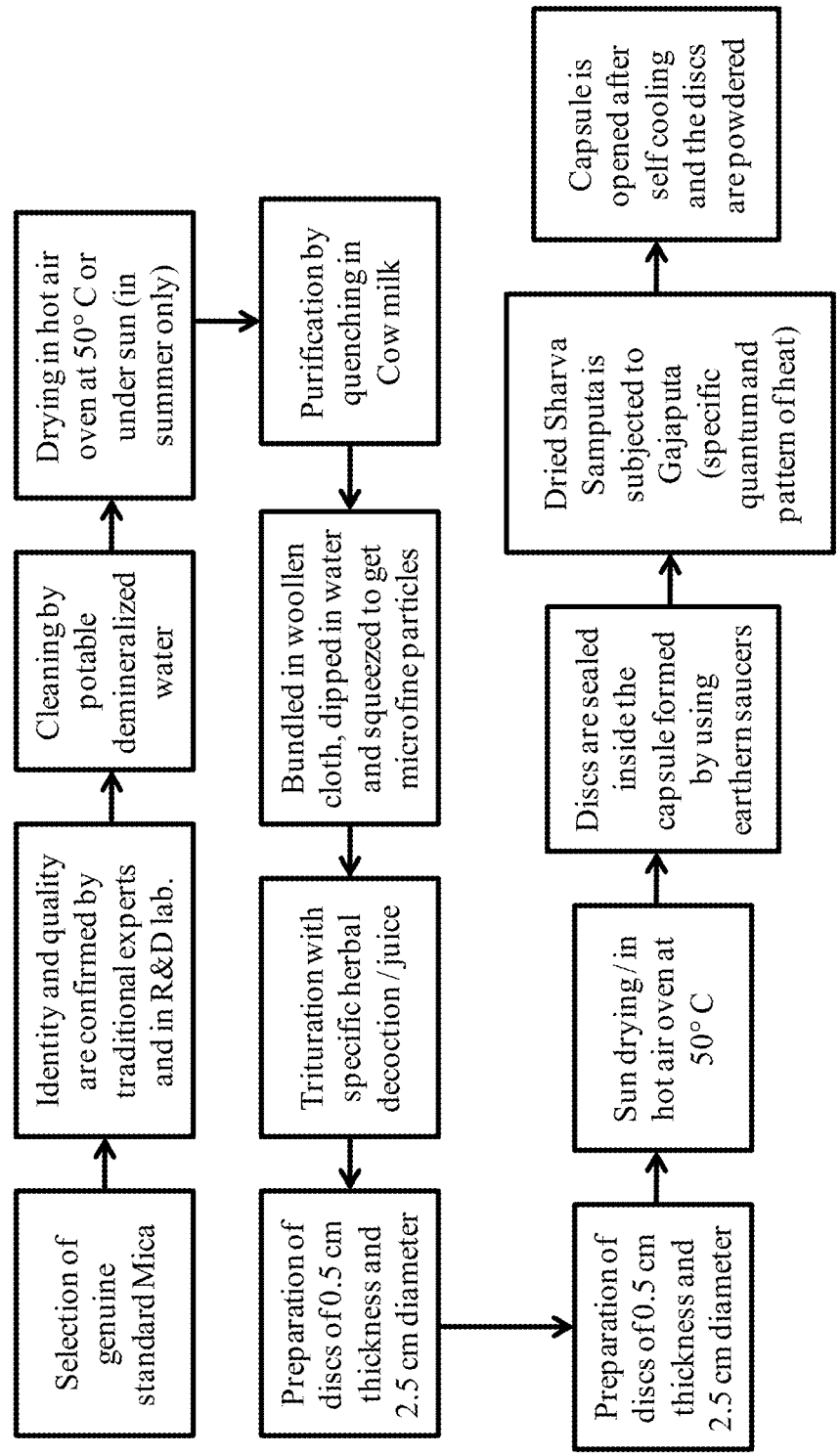
FIG. 1(c) depicts a flowchart for the preparation of Abhraka Bhasma, according to the various embodiments herein.
Figure 1D:
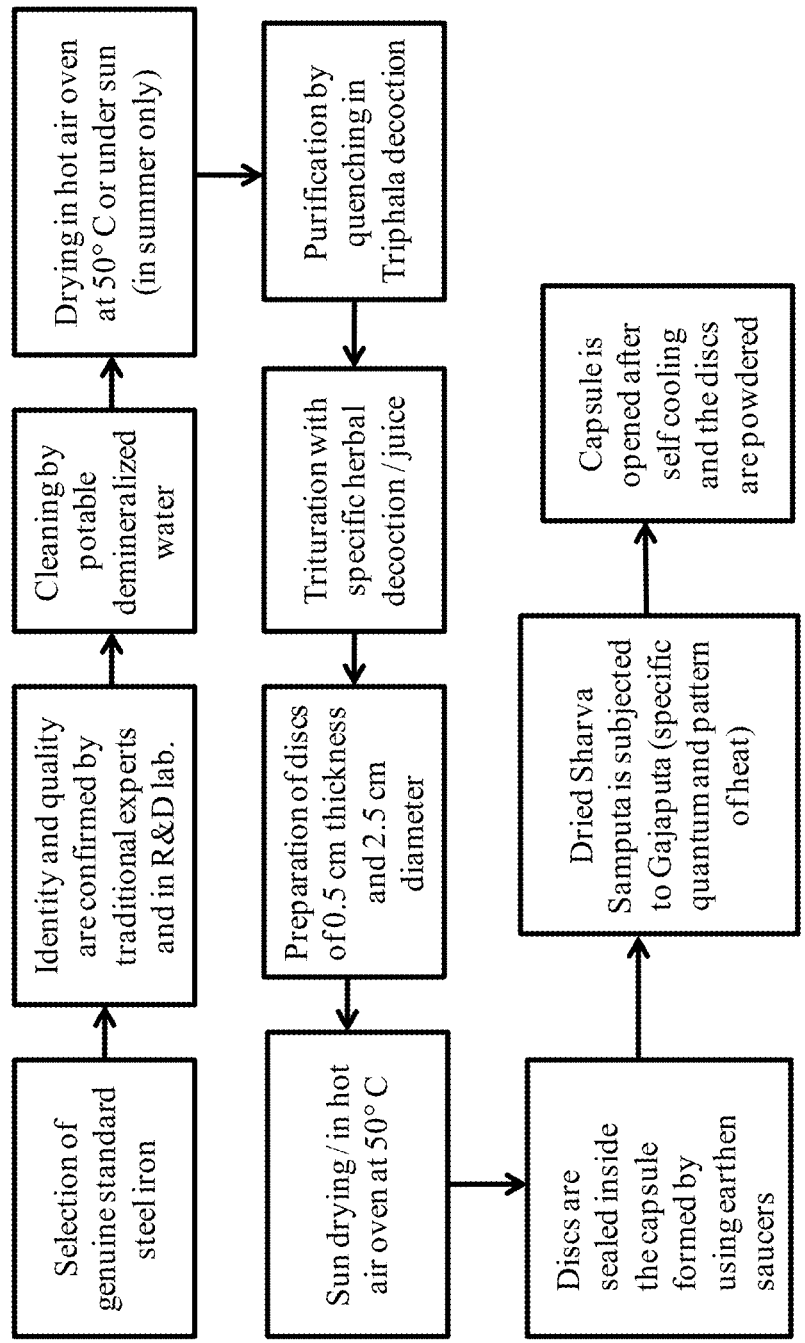
FIG. 1(d) depicts a flowchart for the preparation of Loha Bhasma, according to the various embodiments herein.
Figure 1E:
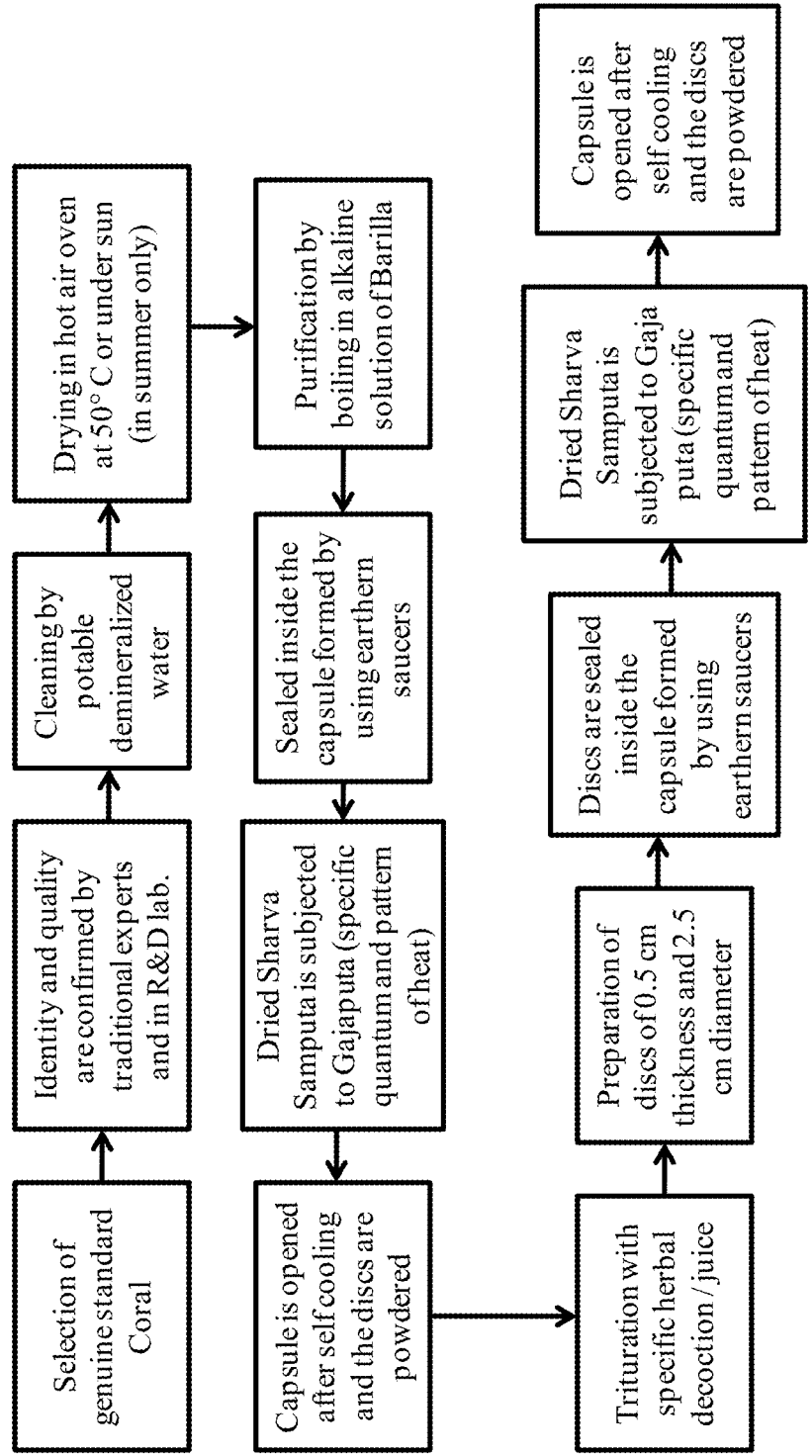
FIG. 1(e) depicts a flowchart for the preparation of Vanga Bhasma, according to the various embodiments herein.
Figure 1F:
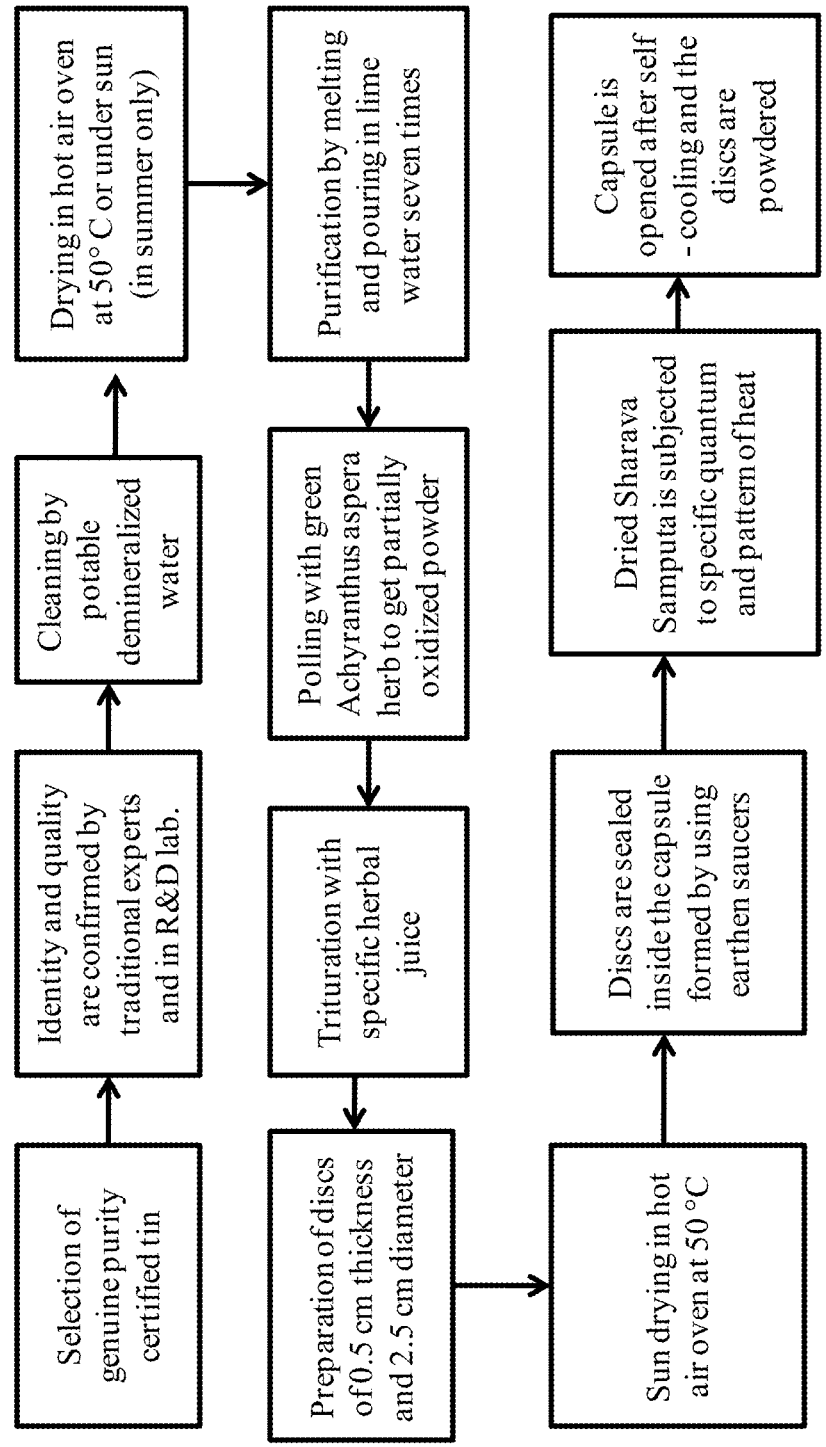
FIG. 1(f) depicts a flowchart for the preparation of Pravala Bhasma, according to the various embodiments herein.
Figure 1G:
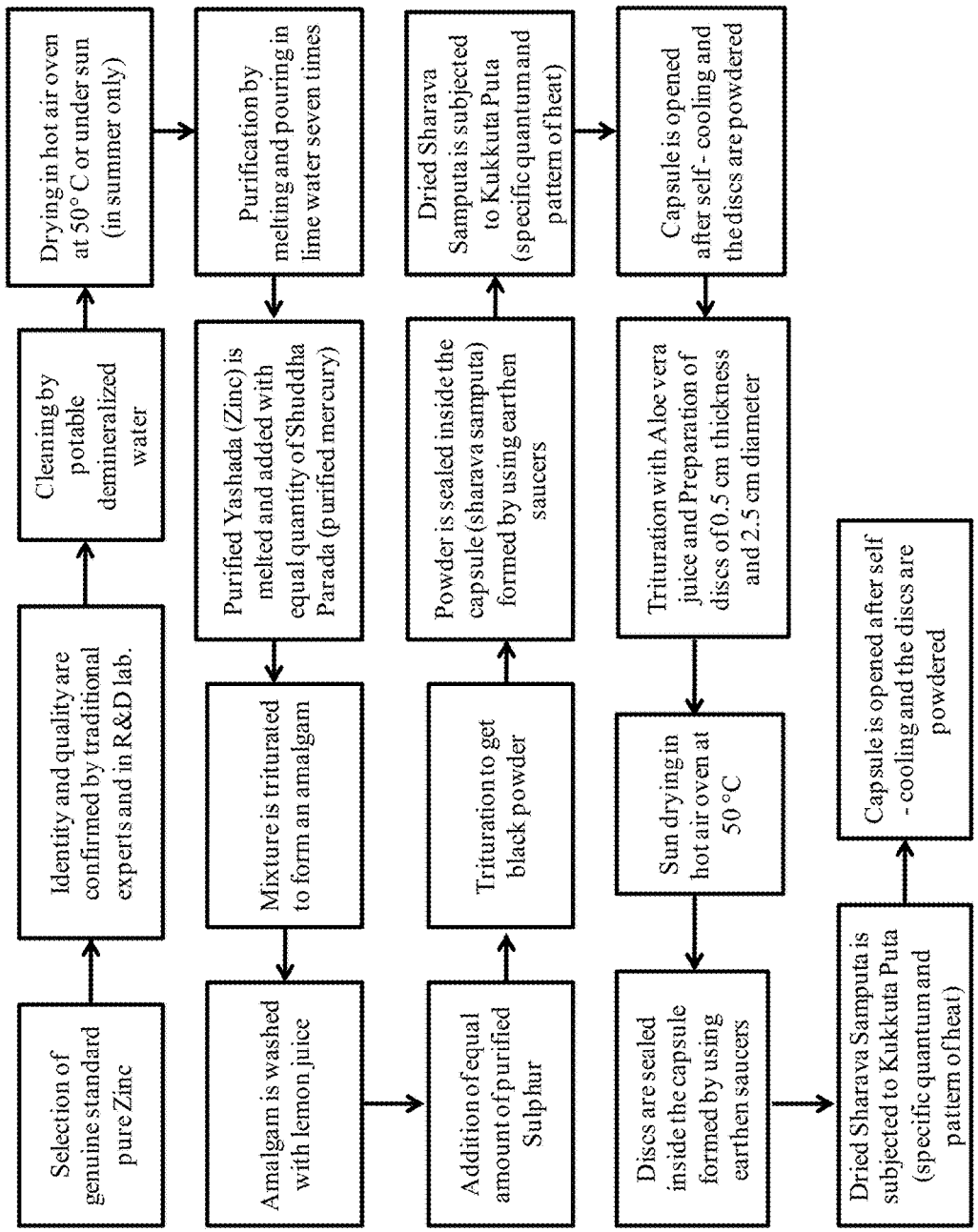
FIG. 1(g) depicts a flowchart for the preparation of Yashada Bhasma, according to the various embodiments herein.

The starting materials used in the preparation of bhasmas may include standard minerals generally used in the field. In an embodiment, the preparation of Swarna Makshika Bhasma includes Swarna makshika as the starting material. FIG. 1(b) depicts a flowchart for the preparation of Swarna Makshika Bhasma using Swarna makshika as the starting material. In an embodiment, the preparation of Abhraka Bhasma includes Mica as the starting material. FIG. 1(c) depicts a flowchart for the preparation of Abhraka Bhasma using Mica as the starting material. In an embodiment, the preparation of Loha Bhasma includes steel iron as the starting material. FIG. 1(d) depicts a flowchart for the preparation of Loha Bhasma using steel iron as the starting material. In an embodiment, the preparation of Pravala Bhasma includes coral as the starting material. FIG. 1(e) depicts a flowchart for the preparation of Pravala Bhasma using coral as the starting material. In an embodiment, the preparation of Vanga Bhasma includes tin as the starting material. FIG. 1(f) depicts a flowchart for the preparation of Vanga Bhasma using tin as the starting material. In an embodiment, the preparation of Yashada Bhasma includes zinc as the starting material. FIG. 1(g) depicts a flowchart for the preparation of Yashada Bhasma using zinc as the starting material.

The purification, or shodhana, of the mineral may be performed by generally known methods in the field. In an embodiment, the purification may be by mixing the mineral, such as Swarna makshika, with rock salt and lemon juice and heating strongly till partially oxidized into reddish powder which may further be used in the preparation of Swarna makshika Bhasma. In another embodiment, the purification may be by quenching a mineral such as mica in Cow's milk, wherein it is further used in the preparation of Abhraka Bhasma. In yet another embodiment, the purification may be by quenching a mineral such as steel iron in Triphala decoction, which is further used in the preparation of Loha Bhasma. In yet another embodiment, the purification may be by melting and pouring a mineral such tin in lime water, preferably seven times, which is further used in the preparation of Vanga Bhasma. Further, in an embodiment, the process of purification may include boiling mineral such as Coral in an alkaline solution of Barilla, which is further used in the preparation of Pravala Bhasma. In yet another embodiment, the purification may be by melting and pouring a mineral such as tin and zinc in lime water, preferably seven times, which is further used in the preparation of bhasmas such as Vanga Bhasma and Yashada bhasma, respectively.

The herbal decoction used may be any herbal decoction that is generally used for triturating in the preparation of bhasmas. In an embodiment, the herbal decoction includes one of more herbal ingredient selected from a group consisting of *Nimbu Swarasa* (Lemon juice) and *Kulatha Kwatha* (Decoction of *Dolichos biflorus*), wherein it is useful in the preparation of Swarna Makshika bhasma. In another embodiment, the herbal decoction specifically includes *Arka Ksheera* (Latex of *calotropis procera*), *Snuhi Ksheera* (Latex of *Euphorbia neriifolia*), *Vata Ksheera* (Latex of *Ficus benghalensis*), *Kakamachi Rasa* (fresh juice of *Solanum nigrum* whole plant), *Gokshura Kwatha* (decoction of *Tribulus terrestris* fruits), *Apamarga Rasa* (Juice of *Achyranthes aspera* plant), *Vata Praroha Swarasa* (juice of aerial root of *Ficus benghalensis*), *Gomutra* (Cow urine), *Tulasi Swarasa* (Fresh juice of *Ocimum sanctum* leaves), *Kadali Shipha Jala* (Juice of plantain rhizome), *Eranda patra rasa* (Juice of *Ricinus communis* leaves), and *Guda* (Jaggery), wherein it is useful in the preparation of Abhraka Bhasma. In an embodiment, the herbal juice specifically includes Aloe vera (fresh juice of leaves) and *Vitex negundo* (fresh juice of leaves), wherein it is useful in the preparation of Vanga Bhasma. In an embodiment, the herbal decoction specifically includes Aloe vera (fresh juice of leaves), *Asparagus racemosus* (fresh juice of roots) and *Sesbania sesban* (fresh juice of leaves), wherein it is useful in the preparation of Pravala Bhasma. Further, in an embodiment, the herbal juice includes a mixture of Aloe vera (fresh juice of leaves), *Asparagus racemosus* (fresh juice of roots) and *Sesbania sesban* (fresh juice of leaves) in cow's milk (Godugdha), wherein it is useful in the preparation of Pravala Bhasma. In another embodiment, the herbal juice specifically includes Aloe vera (fresh juice of leaves) and *Citrus limon* Linn (fresh fruit), wherein it is useful in the preparation of Yashada Bhasma.

Treatment

Disclosed herein are embodiments of a method for the treatment and management of cancer. The embodiments disclosed herein may be used to improve the general health of individuals having a condition involving abnormal and unregulated cell proliferation. Also disclosed are embodiments of a method of inducing cancer cell cytotoxicity and apoptosis. Further, the embodiments disclosed include a method of inducing anti-proliferative and growth inhibitory effect on cancerous cells. The embodiments disclosed herein also include a method for alleviating the side effect of Cancer treatment. In various embodiments, a method for preparing the human body to endure cancer treatment is also provided.

In an embodiment, the method includes administering to a patient a composition as described in any of the embodiments disclosed herein.

The patient, in various embodiments herein, may be any individual in need of such treatment including ones having/expected or suspected of having cancer, tumor, cancer associated complications, side effects of cancer treatment etc. The patient may also include individuals undergoing or preparing to undergo cancer treatment. Further, the patient may also be any individual having a condition involving abnormal and unregulated cell proliferation of any cell type including conditions such as carcinoma of oesophagus, carcinoma of lung, bronchogenic carcinoma, adenocarcinoma of endometrium, adenocarcinoma of rectum, Non-Hodgkin's lymphoma, chronic myeloid leukemia, borderline mucinous tumor, adenocarcinoma of colon, fibro sarcoma, ovarian carcinoma, Cervix Adenocarcinoma, carcinoma of pancreas etc. Experimental studies show significant improvement in cases of Dalton Cell lymphoma. In a specific embodiment, the patient includes an individual having Dalton Cell lymphoma. The patient may further include individuals having undergone prior cancer treatment procedures such as chemotherapy, surgery, or no prior cancer treatment procedures. In another embodiment, the cancer cells include any cells that are cancerous in nature including Human Cervix Adenocarcinoma cells, Human Lung Carcinoma cells, Human Ovarian Cancer cells etc.

In an embodiment, the method for the treatment and management of cancer includes administering to a patient a composition having a herb component, a mineral component and a suitable excipient, wherein the herb component includes *Vinca rosea* (3 to 6 wt %), *Aristolochia indica* (3 to 6 wt %), *Eclipta alba* (3 to 6 wt %), *Moringa oleifera* (3 to 6 wt %), *Curcuma longa* (3 to 6 wt %), *Boerhavia diffusa* (1 to 3 wt %), *Adhatoda vasica* (2 to 4 wt %), *Bauhinia variegata* (≤2 wt %), *Commiphora mukul* (1 to 3 wt %), *Azadirachta indica* (≤2 wt %), *Aconitum heterophyllum* (≤2 wt %), *Smilax china* (≤2 wt %), *Tinospora cordifolia* (≤3 wt %), *Withania somnifera* (1 to 3 wt %), *Sida cordifolia* (1 to 3 wt %), *Terminalia chebula* (≤2 wt %), *Terminalia bellerica* (≤2 w %), *Emblica officinalis* (2 to 4 wt %), *Piper longum* (≤2 wt %), *Piper nigrum* (≤2 wt %), *Zingiber officinalis* (≤2 wt %) and *Ocimum sanctum* (2 to 4 wt %); and the mineral component includes at least one of the following minerals Kajjali (black sulphide of mercury) (0.1 to 20 wt %), shilajit (1 to 3 wt %), Abhraka Bhasma (1 to 3 wt %), Vanga Bhasma (≤2 wt %), Pravala Bhasma (1 to 3 wt %), Loha Bhasma (1 to 3 wt %), Yashada bhasma (≤2 wt %) and Swarna Makshika Bhasma (1 to 3 wt %).

In an embodiment, the method of inducing cancer cell cytotoxicity/apoptosis and/or anti-proliferative/growth inhibitory effect includes administering cancer cells or patient to a composition having a herb component and a mineral component, wherein the herb component includes the following herbs *Vinca rosea* (3 to 6 wt %), *Aristolochia indica* (3 to 6 wt %), *Eclipta alba* (3 to 6 wt %), *Moringa oleifera* (3 to 6 wt %), *Curcuma longa* (3 to 6 wt %), *Boerhavia diffusa* (1 to 3 wt %), *Adhatoda vasica* (2 to 4 wt %), *Bauhinia variegata* (≤2 wt %), *Commiphora mukul* (1 to 3 wt %), *Azadirachta indica* (≤2 wt %), *Aconitum heterophyllum* (≤2 wt %), *Smilax china* (≤2 wt %), *Tinospora cordifolia* (≤3 wt %), *Withania somnifera* (1 to 3 wt %), *Sida cordifolia* (1 to 3 wt %), *Terminalia chebula* (≤2 wt %), *Terminalia bellerica* (≤2 w %), *Emblica officinalis* (2 to 4 wt %), *Piper longum* (≤2 wt %), *Piper nigrum* (≤2 wt %), *Zingiber officinalis* (≤2 wt %) and *Ocimum sanctum* (2 to 4 wt %); and the mineral component includes at least one of the following minerals Kajjali (black sulphide of mercury) (0.1 to 20 wt %), shilajit (1 to 3 wt %), Abhraka Bhasma (1 to 3 wt %), Vanga Bhasma (≤2 wt %), Pravala Bhasma (1 to 3 wt %), Loha Bhasma (1 to 3 wt %), Yashada bhasma (≤2 wt %), and Swarna Makshika Bhasma (1 to 3 wt %).

Disclosed herein is a method to alleviate the side effects of Cancer treatment. In an embodiment, the method of alleviating the side effects of cancer treatment includes administering to a patient an effective amount of the composition disclosed in the various embodiments herein, wherein said patient includes patients having side effect of cancer treatment, patients undergoing cancer treatment, or patients preparing to undergo cancer treatment such as chemotherapy, radiation therapy, hormone therapy, targeted therapy, etc.

The disclosed method of treatment may be used as a primary line of treatment or as an adjunct to other cancer treatment methods. In an embodiment, the method may be instrumental in improving the health conditions of individuals having cancer.

The dosage of the test drug and the treatment regimen may vary depending on the patient. Embodiments of the composition disclosed herein were analyzed for cytotoxicity against selected cell lines. Embodiments of the compositions disclosed herein (also referred to as test drug) is further described by reference to the following examples by way of illustration only and should not be construed to limit the scope of the embodiments herein. The following examples disclose in-vitro analysis of embodiments of the disclosed composition on selected cell lines. It will be apparent to those skilled in the art that many modifications, both to materials and methods, may be practiced without departing from the scope of the claims.

Example 1

Objective:

The purpose of this Study is to evaluate the test substances for their cytotoxicity against selected cell lines.

Summary:

In-vitro cytotoxicity of the test substances Sample II were tested by MTT for A549 (Human Lung Carcinoma), HeLa (Human Cervix Adenocarcinoma), SKOV3 (Human ovarian cancer), CaCo2 (Human Colon carcinoma) and MDA-MB 231 (Human breast cancer) cell lines. The test substances Sample II were taken at concentrations ranging from 1000 µg/ml to 7.8 µg/ml to determine the percentage growth inhibition on the cell lines A549, HeLa, SKOV3, CaCo2 and MDA MB 231. The test substances exhibited a CTC50 value of 117.71±2.37, 202.39±4.25, 94.28±2.06, 155.86±1.03 and 167.47±4.48 respectively Method:

The in vitro cytotoxicity was performed for Sample-II Tablets on A549 (Human Lung Carcinoma), HeLa (Human Cervix Adenocarcinoma) SKOV3 (Human ovarian cancer), CaCo2 (Human Colon carcinoma) and MDA MB 231 (Human breast cancer) cell lines to find toxic concentration of the Sample II by MTT assay.

Preparation of Test Solution:

For cytotoxicity studies, 10 mg of the test substance were separately dissolved and volume was made up with MEM/DMEM-HG supplemented with 2% inactivated FBS to obtain a stock solution of 1 mg/ml concentration and sterilized by 0.22µ syringe filtration. Serial two fold dilutions were prepared from this for carrying out cytotoxic studies.

Cell Line and Culture Medium:

A549 (Human Lung Carcinoma), HeLa (Human Cervix Adenocarcinoma), SKOV3 (Human ovarian cancer), CaCo2 (Human Colon carcinoma) and MDA MB 231 (Human breast cancer) Cell lines were procured from National Centre for Cell Sciences (NCCS), Pune, India. Stock cells were cultured in their respective media viz., MEM/DMEM-HG supplemented with 10% inactivated Fetal Bovine Serum (FBS), penicillin (100 IU/ml), streptomycin (100 µg/ml) and amphotericin B (5 µg/ml) in a humidified atmosphere of 5% $CO_2$ at 37° C. until confluent. The cells were dissociated with TPVG solution (0.2% trypsin, 0.02% EDTA, 0.05% glucose in PBS). The stock cultures were grown in 25 cm2 culture flasks and all experiments were carried out in 96 well microtiter plates (Tarsons India Pvt. Ltd., Kolkata, India).

Cytotoxicity Studies:

In all the cell lines, the monolayer cell culture was trypsinized and the cell count was adjusted to 100,000 cells/ml using respective media viz., MEM/DMEM-HG containing 10% FBS. To each well of the 96 well microtiter plate, 0.1 ml of the diluted cell suspension was added. After 24 h, when a partial monolayer was formed, the supernatant was flicked off, monolayer washed once with medium and 100 µl of different test concentrations of test substances were added on to the partial monolayer in microtiter plates. The plates were then incubated at 37 degree C. for 72 h in 5% $CO_2$ atmosphere, and microscopic examination was carried out and observations were noted every 24 h interval.

MTT Assay:

After 72 h incubation, the drug solutions in the wells were discarded and 50 µl of MTT in PBS was added to each well. The plates were gently shaken and incubated for 3 h at 37 degree C. in 5% $CO_2$ atmosphere. The supernatant was removed and 100 µl of propanol was added and the plates were gently shaken to solubilize the formed formazan. The absorbance was measured using a microplate reader at a wavelength of 540 nm. The percentage growth inhibition was calculated using the standard formula and concentration of test substances needed to inhibit cell growth by 50% (CTC50) values was generated from the dose-response curves for each cell line.

Figure 3:
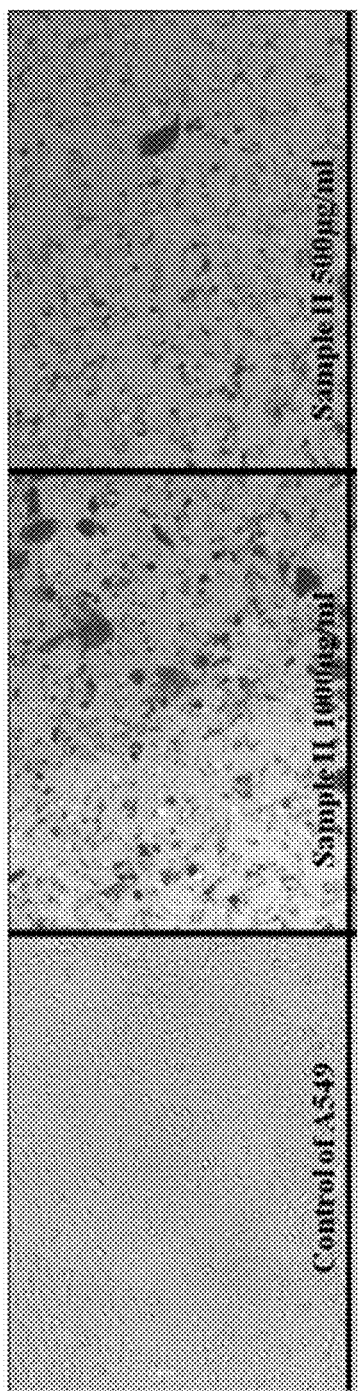
FIG. 3 represents an image illustrating the Cytotoxic effect of test drug on A549 cell line, according to the various embodiments herein.
Figure 8:
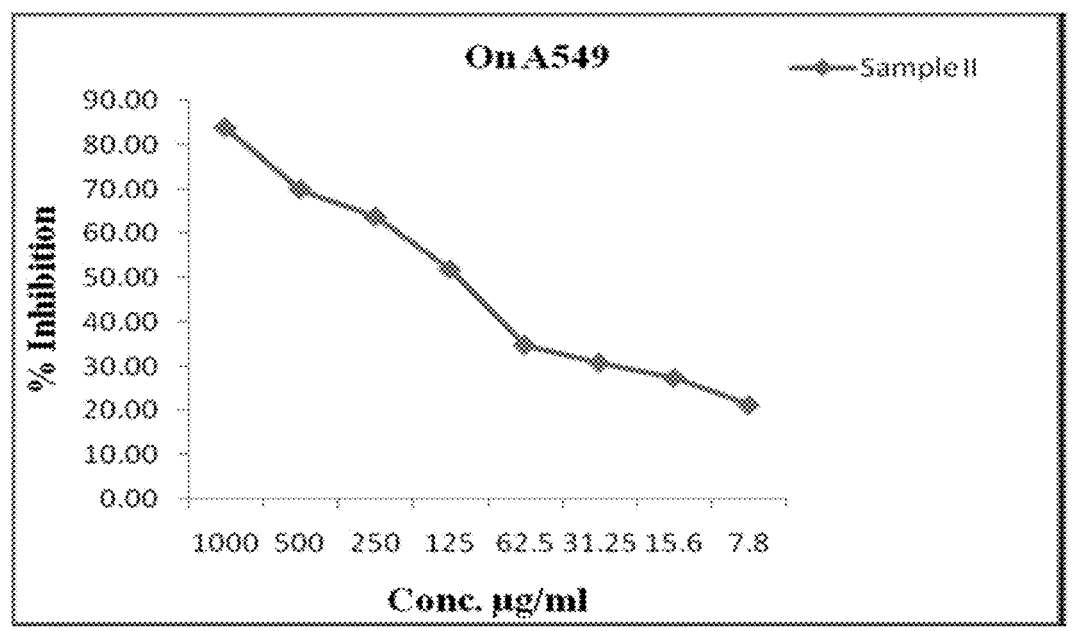
FIG. 8 is a graphical representation illustrating the percentage inhibition of test drug on A549 cell line, according to the various embodiments herein.

Results:

Table 6 depicts the percentage cytotoxicity of test substances against A549 cell line. FIG. 3 illustrates the Cytotoxicity of test drug on A549 cell line. FIG. 8 is a graph depicting the percentage inhibition of test drug on A549 cell line.

TABLE 6

Cytotoxic properties of test substances against A549 cell line.

| Sl. No | Test Conc. (µg/ml) | % Cytotoxicity | CTC50 (µg/ml) |
|---|---|---|---|
| 1. | 1000 | 84.02 ± 0.30 | 117.71 ± 2.37 |
|  | 500 | 70.08 ± 1.81 |  |
|  | 250 | 63.84 ± 0.54 |  |
|  | 125 | 52.02 ± 0.78 |  |
|  | 62.5 | 34.90 ± 0.72 |  |
|  | 31.25 | 30.90 ± 0.58 |  |
|  | 15.6 | 27.52 ± 0.48 |  |
|  | 7.8 | 21.36 ± 0.77 |  |

Figure 4:
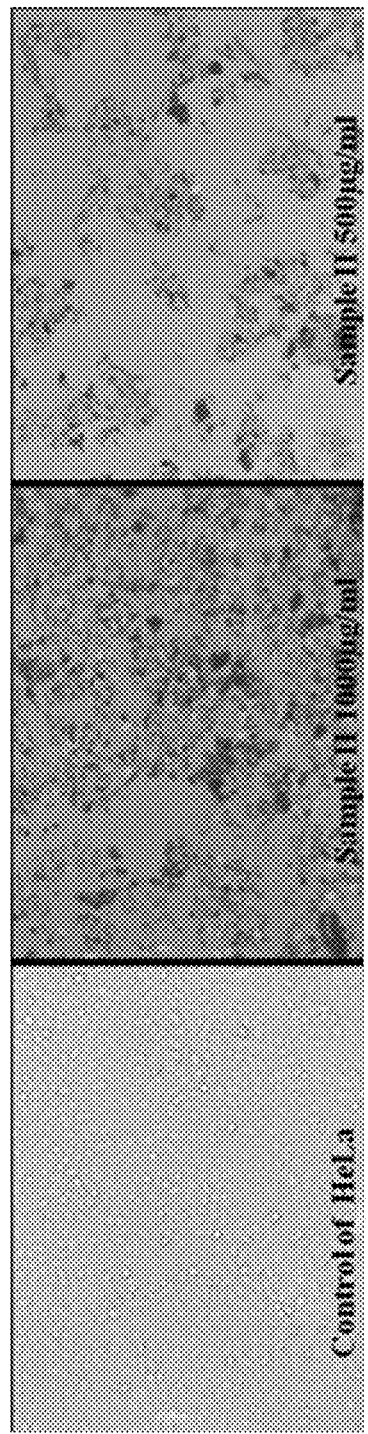
FIG. 4 represents an image illustrating the Cytotoxic effect of test drug on HeLa cell line, according to the various embodiments herein.
Figure 9:
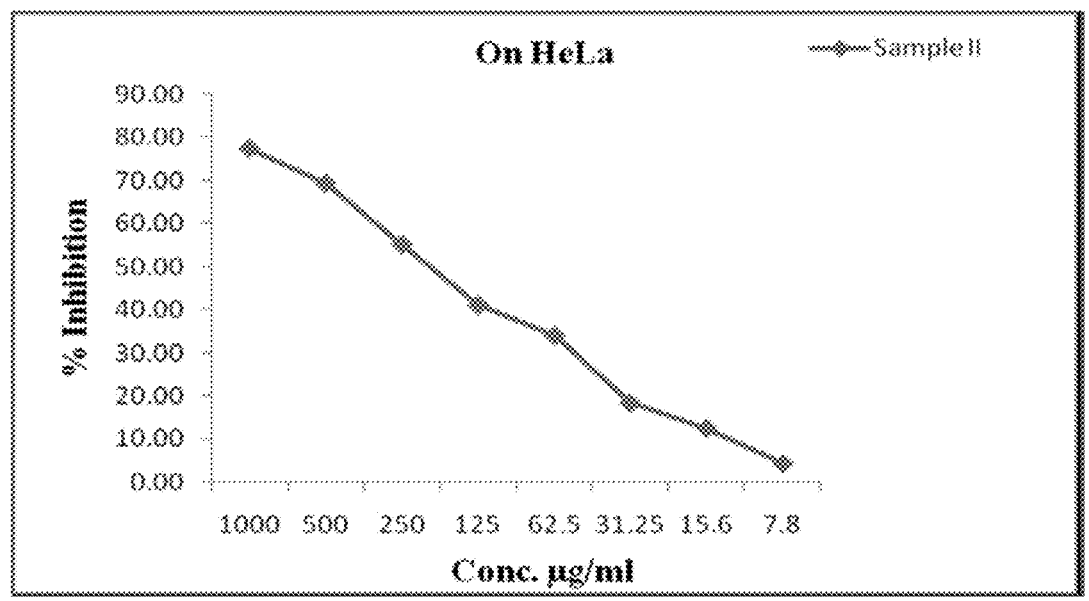
FIG. 9 is a graphical representation illustrating the percentage inhibition of test drug on HeLa cell line, according to the various embodiments herein.

Table 7 depicts the percentage cytotoxicity of test substances against HeLa cell line. FIG. 4 illustrates the Cytotoxicity of test drug on HeLa cell line. FIG. 9 is a graph depicting the percentage inhibition of test drug on HeLa cell line.

TABLE 7

Cytotoxic properties of test substances against HeLa cell line.

| Sl. No | Test Conc. (µg/ml) | % Cytotoxicity | CTC50 (µg/ml) |
| --- | --- | --- | --- |
| 1. | 1000 | 77.33 ± 2.33 | 202.395 ± 4.24 |
|  | 500 | 69.29 ± 4.40 |  |
|  | 250 | 55.12 ± 0.65 |  |
|  | 125 | 41.04 ± 0.39 |  |
|  | 62.5 | 34.00 ± 1.29 |  |
|  | 31.25 | 18.37 ± 0.65 |  |
|  | 15.6 | 12.52 ± 0.65 |  |
|  | 7.8 | 4.39 ± 0.52 |  |

Figure 5:
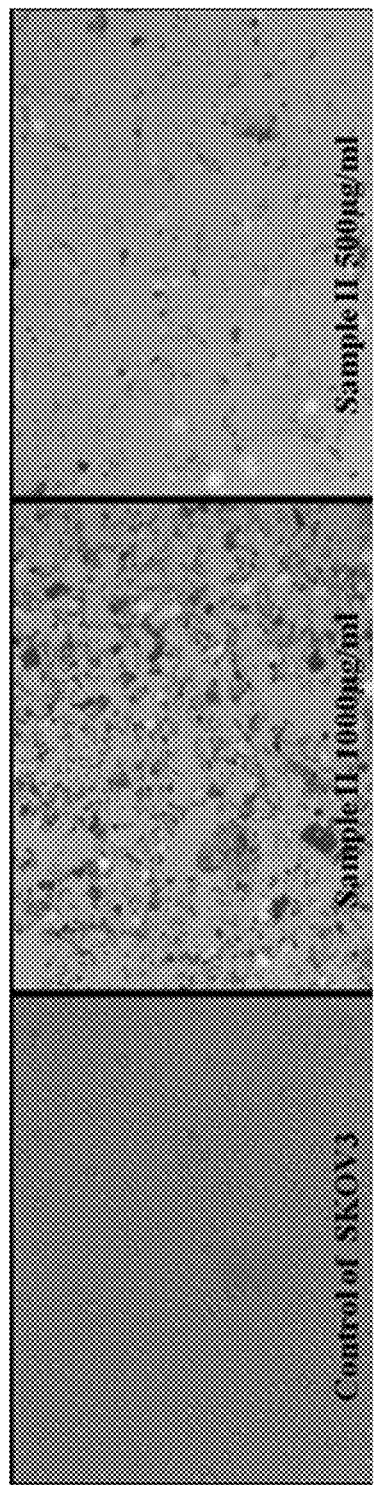
FIG. 5 represents an image illustrating the Cytotoxic effect of test drug on SKOV3 cell line, according to the various embodiments herein.
Figure 10:
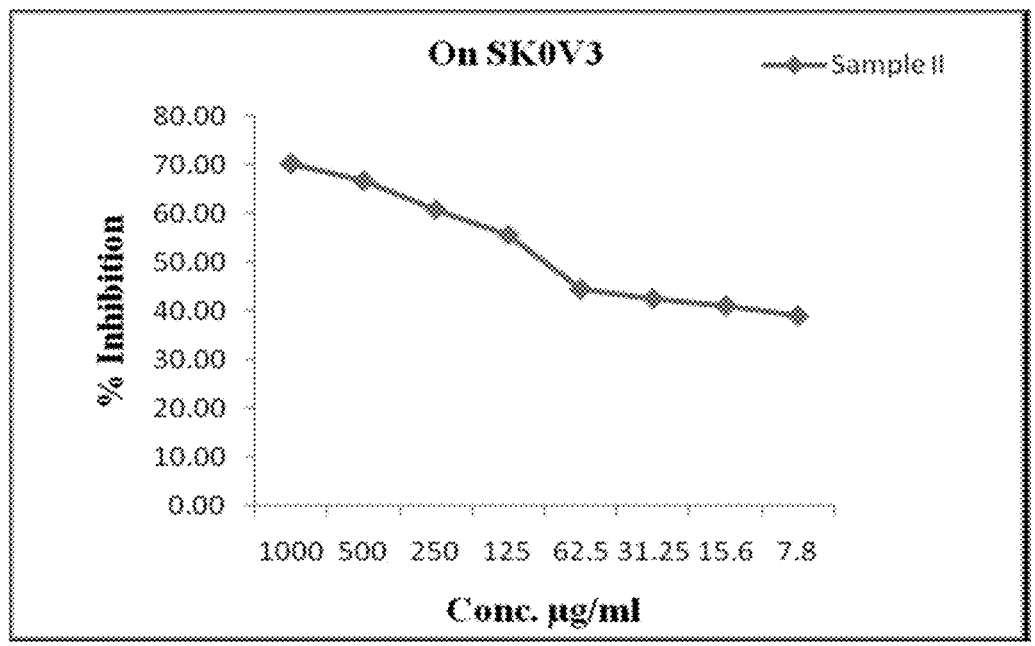
FIG. 10 is a graphical representation illustrating the percentage inhibition of test drug on SKOV3 cell line, according to the various embodiments herein.

Table 8 depicts the percentage cytotoxicity of test substances against SKOV3 cell line. FIG. 5 illustrates the Cytotoxicity of test drug on SKOV3 cell line. FIG. 10 is a graph depicting the percentage inhibition of test drug on SKOV3 cell line.

TABLE 8

Cytotoxic properties of test substances against SKOV3 cell line.

| Sl. No | Test Conc. (µg/ml) | % Cytotoxicity | CTC50 (µg/ml) |
| --- | --- | --- | --- |
| 1. | 1000 | 70.15 ± 0.10 | 94.284 ± 2.06 |
|  | 500 | 66.67 ± 0.39 |  |
|  | 250 | 60.79 ± 0.19 |  |
|  | 125 | 55.60 ± 0.77 |  |
|  | 62.5 | 44.47 ± 0.10 |  |
|  | 31.25 | 42.62 ± 0.39 |  |
|  | 15.6 | 41.12 ± 0.39 |  |
|  | 7.8 | 39.07 ± 0.19 |  |

Figure 6:
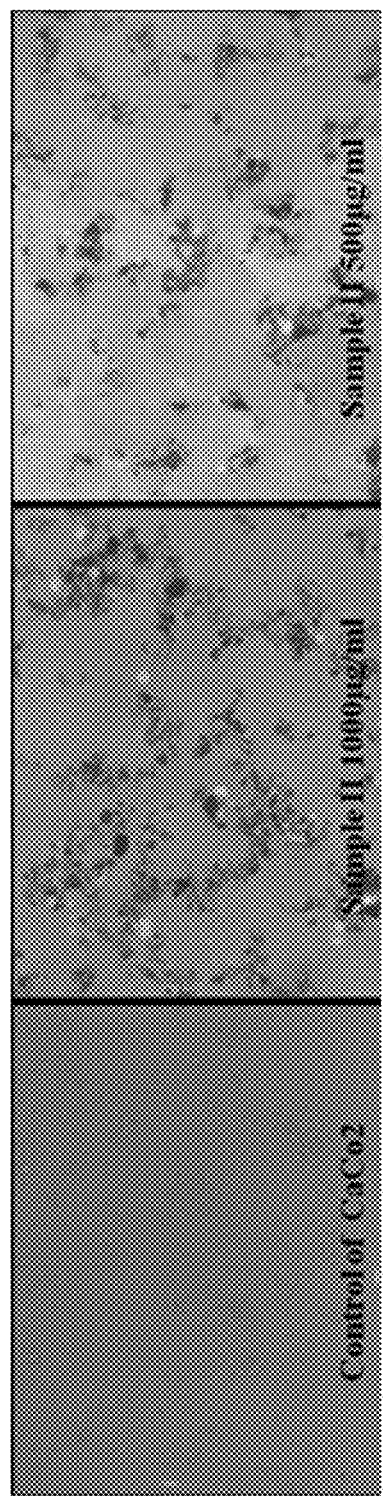
FIG. 6 represents an image illustrating the Cytotoxic effect of test drug on CaCo2 cell line, according to the various embodiments herein.
Figure 11:
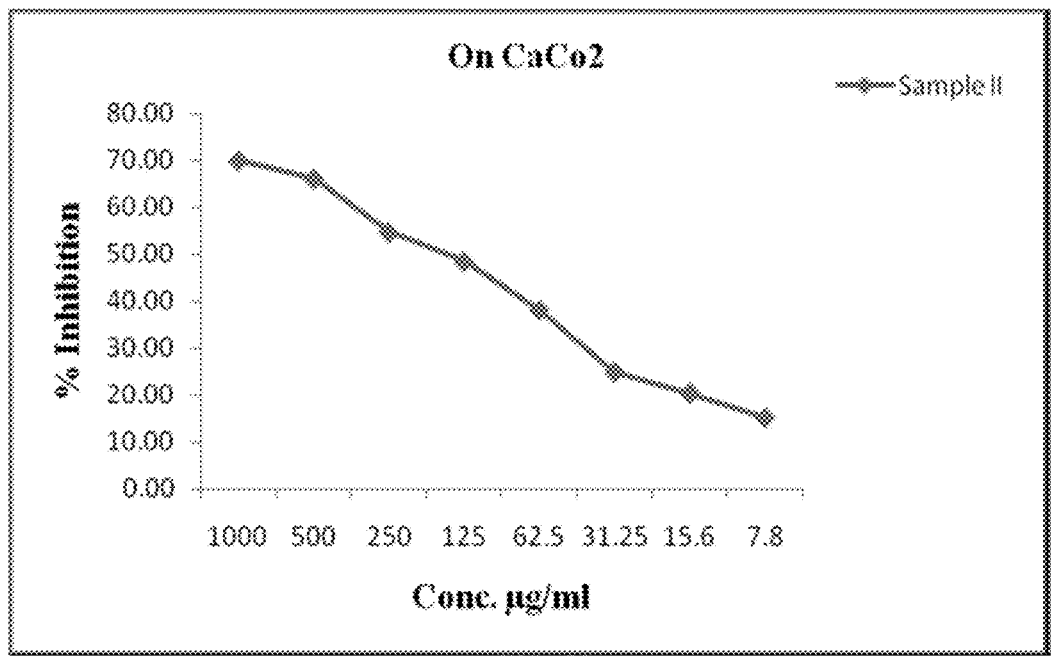
FIG. 11 is a graphical representation illustrating the percentage inhibition of test drug on CaCo2 cell line, according to the various embodiments herein.

Table 9 depicts the percentage cytotoxicity of test substances against CaCo2 cell line. FIG. 6 illustrates the Cytotoxicity of test drug on CaCo2 cell line. FIG. 11 is a graph depicting the percentage inhibition of test drug on CaCo2 cell line.

TABLE 9

Cytotoxic properties of test substances against $CaCO_2$ cell line.

| Sl. No | Test Conc. (µg/ml) | % Cytotoxicity | CTC50 (µg/ml) |
| --- | --- | --- | --- |
| 1. | 1000 | 69.92 ± 0.70 | 155.86 ± 4.03 |
|  | 500 | 66.08 ± 0.41 |  |
|  | 250 | 54.69 ± 0.90 |  |
|  | 125 | 48.44 ± 0.52 |  |
|  | 62.5 | 38.22 ± 1.49 |  |
|  | 31.25 | 25.00 ± 2.40 |  |
|  | 15.6 | 20.51 ± 0.90 |  |
|  | 7.8 | 15.23 ± 1.19 |  |

Figure 7:
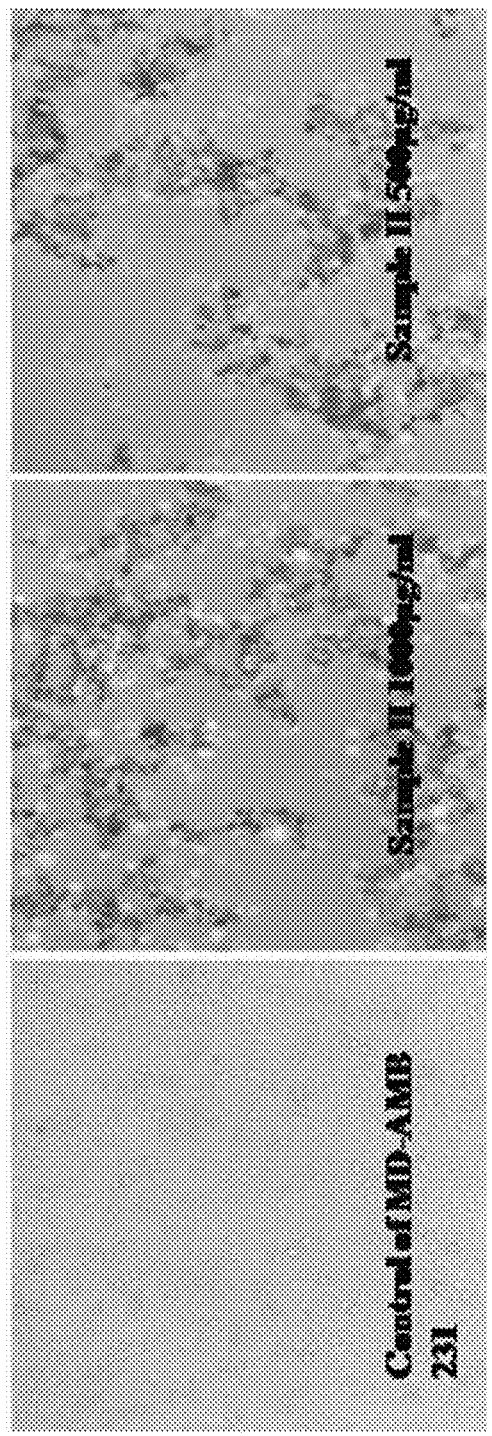
FIG. 7 represents an image illustrating the Cytotoxic effect of test drug on MDA-MB 231 cell line, according to the various embodiments herein.
Figure 12:
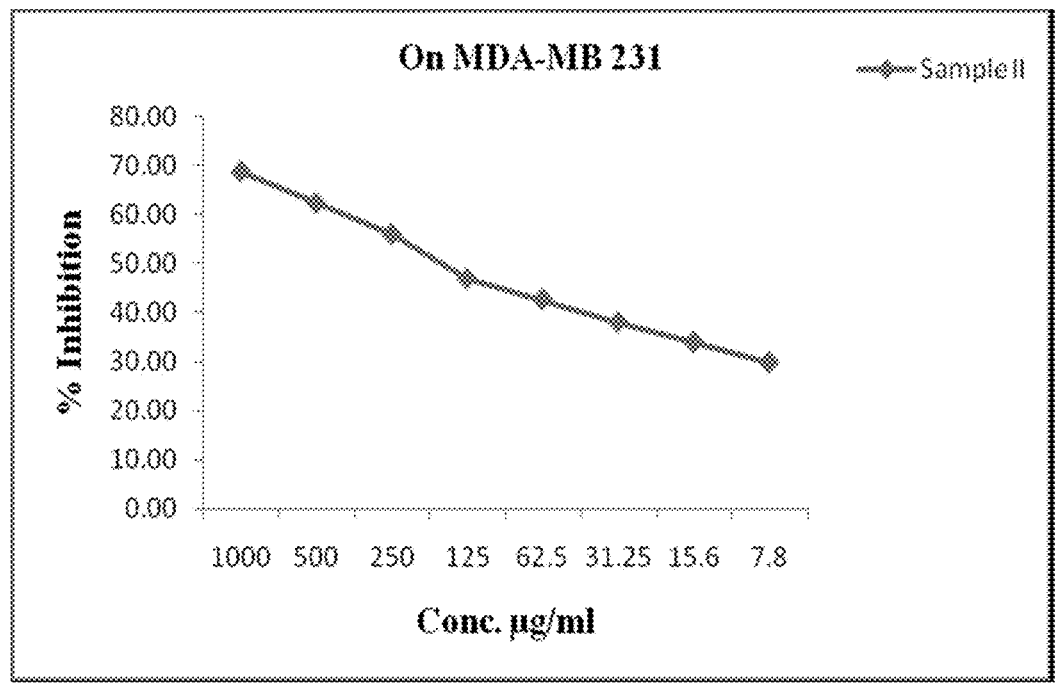
FIG. 12 is a graphical representation illustrating the percentage inhibition of test drug on MDA-MB 231 cell line, according to the various embodiments herein.

Table 10 depicts the percentage cytotoxicity of test substances against MDA MB 231 cell line. FIG. 7 illustrates the Cytotoxicity of test drug on MDA-MB 231 cell line. FIG. 12 is a graph depicting the percentage inhibition of test drug on MDA-MB 231 cell line.

TABLE 10

Cytotoxic properties of test substances against MDA MB 231 cell line.

| Sl. No | Test Conc. (µg/ml) | % Cytotoxicity | CTC50 (µg/ml) |
| --- | --- | --- | --- |
| 1. | 1000 | 68.73 ± 1.64 | 167.47 ± 4.48 |
|  | 500 | 62.26 ± 0.71 |  |
|  | 250 | 56.02 ± 0.34 |  |
|  | 125 | 46.90 ± 0.36 |  |
|  | 62.5 | 42.63 ± 0.34 |  |
|  | 31.25 | 38.05 ± 0.56 |  |
|  | 15.6 | 33.92 ± 0.54 |  |
|  | 7.8 | 29.83 ± 2.29 |  |

Conclusion:

The test substances Sample II were tested for in vitro cytotoxicity against A549 (Human Lung Carcinoma), HeLa (Human Cervix Adenocarcinoma), SKOV3 (Human ovarian cancer), CaCo2 (Human Colon carcinoma) and MDA MB 231 (Human breast cancer) cells by MTT assay, exposing the cells to different concentrations of test substance.

The test substances were taken at concentrations ranging from 1000 µg/ml to 7.8 µg/ml to determine the percentage growth inhibition on the cell lines A549, HeLa, SKOV3, CaCo2 and MDA-MB 231. The test substance Sample II exhibited a CTC50 value of 117.71±2.37, 202.39±4.25, 94.28±2.06, 155.86±4.03 and 167.47±4.48 on A549, HeLa SKOV3, CaCo2 and MDA-MB 231 cell lines respectively.

The test drug was found to have marked cytotoxicity against all the tested cancer cell lines especially against SKOV3 ovarian cancer cell lines.

Example 2: In Vitro Cytotoxicity Study of Test Drug on HepG2 Cell Line

Summary: In-vitro cytotoxicity of the drug Sample II was tested against Human Liver carcinoma cell line. Test substance was taken at concentrations ranging from 1000 to 7.8 µg/ml to determine the percentage growth inhibition of the drug on HepG2 cell line. The drug Sample II exhibited a CTC50 value of >1000.

Table 11 depicts the percentage cytotoxicity of test substances against HepG2 cell line.

TABLE 11

Cytotoxic properties of test substances against HepG2 cell line.

| Sl. No | Name of Test Substance | Test Conc. (µg/ml) | % Cytotoxicity | CTC50 (µg/ml) |
| --- | --- | --- | --- | --- |
| 1. | Test drug | 1000 | 15.82 ± 2.18 | >1000 |
|  |  | 500 | 11.14 ± 0.81 |  |
|  |  | 250 | 8.33 ± 0.86 |  |
|  |  | 125 | 6.27 ± 0.71 |  |
|  |  | 62.5 | 5.06 ± 0.28 |  |
|  |  | 31.25 | 3.65 ± 0.74 |  |
|  |  | 15.6 | 1.97 ± 0.56 |  |
|  |  | 7.8 | 1.12 ± 0.56 |  |

Example 3: In Vitro Cytotoxicity Studies of Test Product on Pancreatic and Hepatic Cancer Cell Lines Objective:

In vitro cytotoxicity study of test drug on panc-1 cell line.

Summary:

In-vitro cytotoxicity of the test drug was tested against Human Pancreatic carcinoma cell line. Test drug was taken at concentrations ranging from 1000 to 7.8 µg/ml to determine the percentage growth inhibition of the drug on PANC-1 cell line. The drug Sample II exhibited a CTC50 value of >1000.

Table 12 depicts the percentage cytotoxicity of test substances against PANC-1 cell line.

TABLE 12

Cytotoxic properties of test substances against PANC-1 cell line.

| Sl. No | Name of Test Substance | Test Conc. (µg/ml) | % Cytotoxicity | CTC50 (µg/ml) |
|---|---|---|---|---|
| 1. | Test drug | 1000 | 20.33 ± 0.66 | >1000 |
| | | 500 | 17.69 ± 0.32 | |
| | | 250 | 10.58 ± 0.57 | |
| | | 125 | 7.69 ± 0.66 | |
| | | 62.5 | 6.11 ± 0.33 | |
| | | 31.25 | 4.16 ± 0.81 | |
| | | 15.6 | 1.63 ± 0.24 | |
| | | 7.8 | 0.53 ± 0.24 | |

Example 3: Evaluation of In Vitro Cytotoxicity of Test Product on AGS and MIA PACA Cells Objective: In-vitro cytotoxicity study of test drug on AGS and MIA PACA cells.

Figure 13:
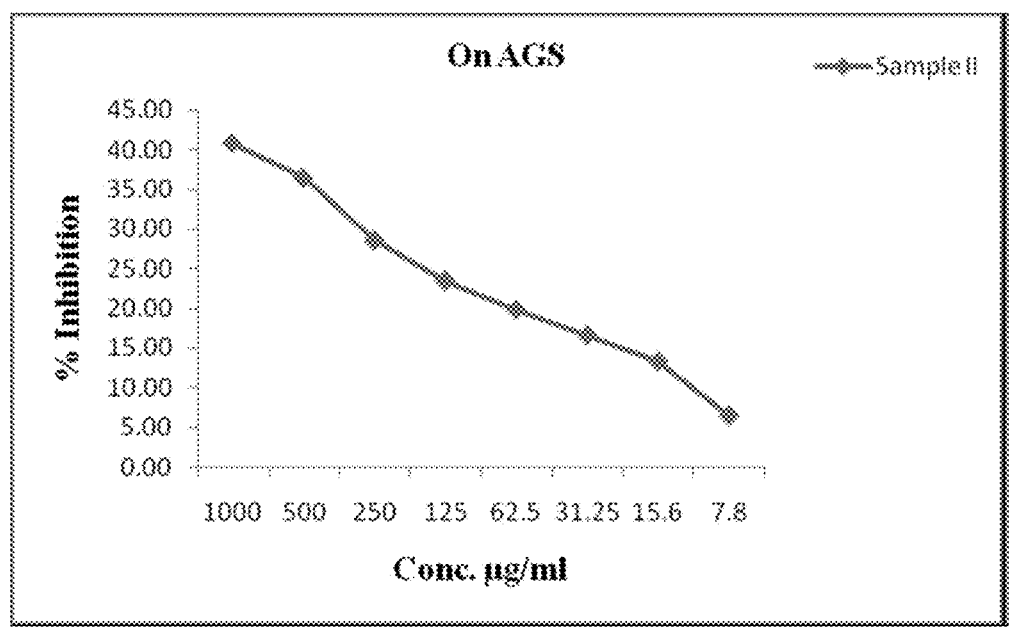
FIG. 13 is a graphical representation illustrating the percentage inhibition of test drug on AGS cell line, according to the various embodiments herein.

Summary:

In-vitro cytotoxicity of the drug Sample was tested against Human Gastric cancer (AGS) and Human Pancreatic Cancer cell line (MIA PACA). Drugs were taken at concentrations ranging from 1000 to 7.8 µg/ml to determine the percentage growth inhibition of the drug on AGS and MIA PACA cell line. The drug Sample II exhibited a CTC50 value of >1000 and 809.96±4.29 on AGS and MIA PACA cell lines, respectively. Table 13 depicts the percentage Cytotoxicity of test drug against AGS cell line. FIG. 13 is a graph showing percentage inhibition of test drug on AGS cell line.

TABLE 13

Cytotoxicity of test drug against AGS cell line.

| No | Name of Test Substance | Test Conc. (µg/ml) | % Cytotoxicity | CTC50 (µg/ml) |
|---|---|---|---|---|
| 1. | Test drug | 1000 | 40.78 ± 0.71 | >1000 |
| | | 500 | 36.45 ± 1.90 | |
| | | 250 | 28.60 ± 0.34 | |
| | | 125 | 23.47 ± 0.34 | |
| | | 62.5 | 19.83 ± 1.04 | |
| | | 31.25 | 16.64 ± 1.02 | |
| | | 15.6 | 13.34 ± 1.04 | |
| | | 7.8 | 6.50 ± 1.61 | |

Figure 14:
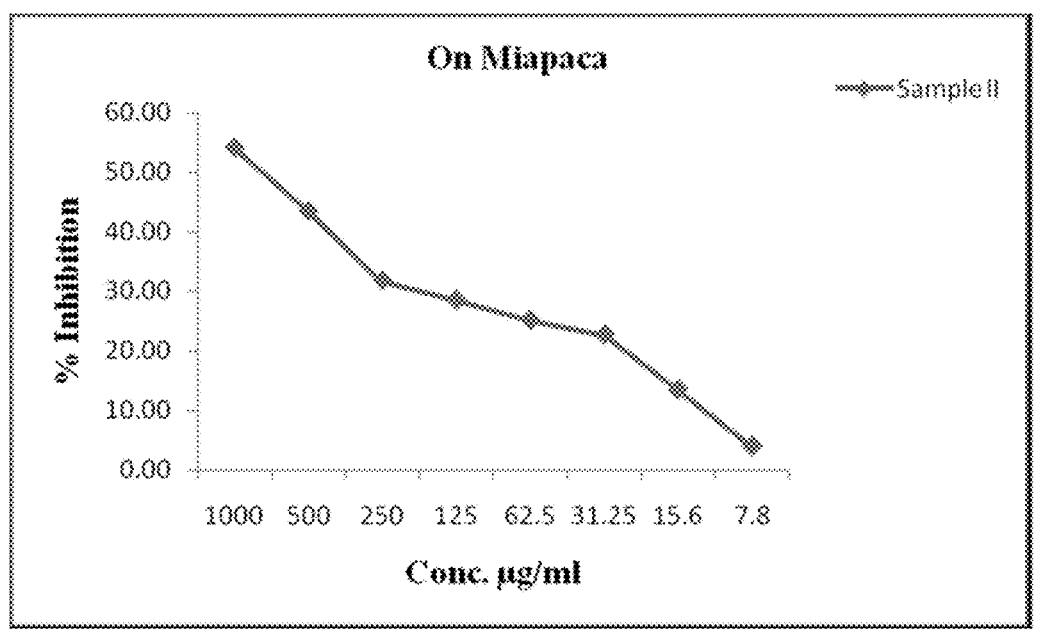
FIG. 14 is a graphical representation illustrating the percentage inhibition of test drug on MIA PACA cell line, according to the various embodiments herein.

Table 14 depicts the percentage Cytotoxicity of test drug against MIA PACA cell line. FIG. 14 is a graph showing percentage inhibition of test drug on MIA PACA cell line.

TABLE 14

Cytotoxicity of test drug against MIA PACA cell line.

| No | Name of Test Substance | Test Conc. (µg/ml) | % Cytotoxicity | CTC50 (µg/ml) |
|---|---|---|---|---|
| 1. | Test drug | 1000 | 54.04 ± 0.61 | >809.96 ± 4.29 |
| | | 500 | 43.44 ± 0.77 | |
| | | 250 | 31.71 ± 0.31 | |
| | | 125 | 28.45 ± 0.93 | |
| | | 62.5 | 25.09 ± 1.07 | |
| | | 31.25 | 22.64 ± 0.93 | |
| | | 15.6 | 13.47 ± 0.77 | |
| | | 7.8 | 3.99 ± 1.24 | |

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral composition comprising *Vinca rosea*, *Aristolochia indica*, *Eclipta alba*, *Moringa oleifera*, *Curcuma longa* and a therapeutically effective amount of Kajjali; wherein said composition is in a form selected from a group consisting of tablets, pellets, lozenges, granules, suspensions and capsules.

2. The oral composition as claimed in claim 1, wherein *Vinca rosea* is present in an amount ranging from 3 to 6 wt % of the total composition.

3. The oral composition as claimed in claim 1, wherein *Aristolochia indica* is present in an amount ranging from 3 to 6 wt % of the total composition.

4. The oral composition as claimed in claim 1, wherein *Eclipta alba* is present in an amount ranging from 3 to 6 wt % of the total composition.

5. The oral composition as claimed in claim 1, wherein *Moringa oleifera* is present in an amount ranging from 3 to 6 wt % of the total composition.

6. The oral composition as claimed in claim 1, wherein *Curcuma longa* is present in an amount ranging from 3 to 6 wt % of the total composition.

7. The oral composition as claimed in claim 1, wherein Kajjali is present in an amount ranging from 0.1 to 20 wt % of the total composition.

8. The oral composition as claimed in claim 1, further comprising at least one ingredient selected from a group consisting of *Boerhavia diffusa*, *Adhatoda vasica*, *Bauhinia variegata*, *Commiphora mukul*, *Azadirachta indica*, *Aconitum heterophyllum*, *Smilax china*, *Tinospora cordifolia*, *Withania somnifera*, *Sida cordifolia*, *Terminalia chebula*, *Terminalia bellerica*, *Emblica officinalis*, *Tinospora cordifolia*, *Piper longum*, *Piper nigrum*, *Zingiber officinalis* and *Ocimum sanctum*.

9. The oral composition as claimed in claim 1, further comprising at least one ingredient selected from a group consisting of

*Boerhavia diffusa* present in an amount ranging from 1 to 3 wt %,

*Adhatoda vasica* present in an amount ranging from 2 to 4 wt %,
*Bauhinia variegata* present in an amount of ≤2 wt %,
*Commiphora mukul* present in an amount ranging from 1 to 3 wt %,
*Azadirachta indica* present in an amount of ≤2 wt %,
*Aconitum heterophyllum* present in an amount of ≤2 wt %,
*Smilax china* present in an amount of ≤2 wt %,
*Tinospora cordifolia* present in an amount ranging from 1 to 3 wt %,
*Withania somnifera* present in an amount ranging from 1 to 3 wt %,
*Sida cordifolia* present in an amount ranging from 1 to 3 wt %,
*Terminalia chebula* present in an amount of ≤2 wt %,
*Terminalia bellerica* present in an amount of ≤2 wt %,
*Emblica officinalis* present in an amount ranging from 2 to 4 wt %,
*Tinospora cordifolia* present in an amount of ≤2 wt %,
*Piper longum* present in an amount of ≤2 wt %,
*Piper nigrum* present in an amount of ≤2 wt %,
*Zingiber officinalis* present in an amount of ≤2 wt % and
*Ocimum sanctum* present in an amount ranging from 2 to 4 wt %,
of the total composition.

10. The oral composition as claimed in claim 1, further comprising *Asphaltum punjabianum* (Shilajit) in an amount ranging from 1 to 3 wt % of the total composition.

11. The oral composition as claimed in claim 1, further comprising at least one bhasma selected from a group consisting of Vanga Bhasma, Yashada Bhasma, Swarna Makshika bhasma, Abhraka Bhasma, Loha bhasma, and Pravala bhasma.

12. The oral composition as claimed in claim 1, further comprising at least one bhasma selected from a group consisting of
Vanga Bhasma present in an amount of ≤2 wt %,
Yashada Bhasma present in an amount of ≤2 wt %,
Swarna Makshika bhasma present in an amount ranging from 1 to 3 wt %,
Abhraka Bhasma present in an amount ranging from 1 to 3 wt %,
Loha bhasma present in an amount ranging from 1 to 3 wt % and
Pravala bhasma present in an amount ranging from 1 to 3 wt %,
of the total composition.

13. An oral composition comprising
*Vinca rosea* in an amount of 4.8 wt %,
*Aristolochia indica* in an amount of 4.8 wt %,
*Eclipta alba* in an amount of 4.8 wt %,
*Moringa oleifera* in an amount of 4.8 wt %,
*Curcuma longa* in an amount of 4.8 wt %,
Kajjali in an amount of 20 wt %,
*Boerhavia diffusa* in an amount of 2.4 wt. %,
*Adhatoda vasica* in an amount of 3.2 wt %,
*Bauhinia variegata* in an amount of 1.6 wt %,
*Commiphora mukul* in an amount of 2.4 wt %,
*Azadirachta indica* in an amount of 1.6 wt %,
*Aconitum heterophyllum* in an amount of 1.6 wt %,
*Smilax china* in an amount of 1.6 wt %,
starch extract of stem of *Tinospora cordifolia* in an amount of 2.4 wt %,
dried stem of *Tinospora cordifolia* in an amount of 1.6 wt %,
*Withania somnifera* in an amount of 2.4 wt %,
*Sida cordifolia* in an amount of 2.4 wt %,
*Terminalia chebula* in an amount of 0.8 wt %,
*Terminalia bellerica* in an amount of 0.8 wt %,
*Emblica officinalis* in an amount of 3.2 wt %,
*Tinospora cordifolia* in an amount of 1.6 wt %,
*Piper longum* in an amount of 0.8 wt %,
*Piper nigrum* an amount of 0.8 wt %,
*Zingiber officinalis* in an amount of 0.8 wt %,
*Ocimum sanctum* in an amount of 3.2 wt %,
Shilajit in an amount of 2.4 wt %,
Vanga Bhasma in an amount of 1.2 wt %,
Yashada Bhasma in an amount of 1.2 wt %,
Swarna Makshika bhasma in an amount of 2.4 wt %,
Abhraka Bhasma in an amount of 2.4 wt %,
Loha bhasma in an amount of 2.4 wt %,
Pravala bhasma in an amount of 2.4 wt %,
of the total composition and a suitable excipient; wherein said composition is in a form selected from a group consisting of tablets, pellets, lozenges, granules, suspensions and capsules.

14. The oral composition as claimed in claim 13, wherein said suitable excipient is gum acacia present in an amount of 8 wt % of the total composition.

15. The oral composition as claimed in claim 14, wherein said composition is in the form of a tablet.

16. The oral composition as claimed claim 15, wherein said tablet is in the form of a 500 mg tablet.

17. A process for the preparation of composition claimed in claim 1, comprising:
levigating processed Kajjali;
adding finely powdered herbs; and
adding grinding decoction while continuing grinding to obtain the composition.

18. A process for the preparation of composition claimed in claim 1, comprising:
levigating processed Kajjali, bhasmas and shilajit;
adding finely powdered herbs; and
adding grinding decoction while continuing grinding to obtain the composition.

19. The process for the preparation of a composition as claimed in claim 18, wherein said bhasmas are selected from a group consisting of Vanga Bhasma, Yashada Bhasma, Swarna Makshika bhasma, Abhraka Bhasma, Loha bhasma, and Pravala bhasma.

20. The process for the preparation of a composition as claimed in claim 17, wherein said finely powdered herbs comprises *Vinca rosea* (dry leaves), *Aristolochia indica* (dry root), *Eclipta alba* (dry whole plant), *Moringa oleifera* (dry stem bark) and *Curcuma longa* (dry rhizome).

21. The process for the preparation of a composition as claimed in claim 17, wherein said finely powdered herbs further comprises *Boerhavia diffusa* (dry root), *Adhatoda vasica* (dry root), *Bauhinia variegata* (dry stem bark), *Commiphora mukul* (oleo gum resin), *Azadirachta indica* (dry stem bark), *Aconitum heterophyllum* (dry root), *Smilax china* (dry root), *Tinospora cordifolia* (starch extract of stem), *Withania somnifera* (dry root), *Sida cordifolia* (dry root), *Terminalia chebula* (dry fruits), *Terminalia bellerica* (dry fruit), *Emblica officinalis* (dry fruits), *Tinospora cordifolia* (dry stem), *Piper longum* (dry fruits), *Piper nigrum* (dry fruits), *Zingiber officinalis* (dry rhizome) and *Ocimum sanctum* (dry leaves).

22. The process for the preparation of a composition as claimed in claim 17, wherein said grinding decoction is a decoction of at least one herb selected from the group consisting of *Aegle marmelos, Premna mucronata, Oroxylum indicum, Steriospermum suaveolens, Gmelina arborea, Solanum indicum, Solanum xanthocarpum, Tribulus ter-*

*restris, Uraria picta, Desmodium gangeticum, Vinca rosea, Ocimum sanctum, Asparagus racemosus, Semecarpus anacardium, Momordica charantia, Eclipta alba, Moringa oleifera, Acacia catechu, Rubia cordifolia, Adhatoda vasica, Bauhinia variegata, Cynadon dactylon, Tinospora cordifolia, Crotolaria juncea, Cuminum cyminum, Smilax china, Mimosa pudica, Calatropis procera, Murraya koeinigi, Trichosanthes dioica* and *Sida cordifolia.*

23. The process for the preparation of a composition as claimed in claim 17, wherein said process further includes mixing the obtained composition with gum acacia and grinding for a period of 1 to 4 hours; and drying at a temperature in the range of 40 to 60° C.

24. A method of inducing cytotoxic or growth inhibitory effect on cancer cells, comprising administering to a patient an effective amount of the composition claimed in claim 1.

25. A method of alleviating the side effects of Cancer treatment, comprising administering to a patient an effective amount of the composition claimed in claim 1.

26. A method for the treatment and management of cancer, comprising administering to a patient an effective amount of the composition claimed in claim 1.

27. The method for the treatment and management of cancer as claimed in claim 26, wherein said effective amount is in the range of 500 mg to 1000 mg per day.

28. The method for the treatment and management of cancer as claimed in claim 26, wherein said cancer is at least one condition selected from a group consisting of carcinoma of oesophagus, carcinoma of lung, bronchogenic carcinoma, adenocarcinoma of endometrium, adenocarcinoma of rectum, Non-Hodgkin's lymphoma, chronic myeloid leukemia, borderline mucinous tumor, adenocarcinoma of colon, fibro sarcoma, ovarian carcinoma, Cervix Adenocarcinoma and carcinoma of pancreas.

29. The method for the treatment and management of cancer as claimed in claim 26, wherein said composition is administered along with administration of at least one other cancer medication.

\* \* \* \* \*